US009017673B2

(12) United States Patent
Baudy et al.

(10) Patent No.: US 9,017,673 B2
(45) Date of Patent: Apr. 28, 2015

(54) PEPTIDE ANALOGUES COMPRISING AT LEAST ONE TYPE OF AMINOACYLAZA-$G(B)^3$ AND THE USE THEREOF, IN PARTICULAR FOR THERAPY

(75) Inventors: Michèle Floc'h Baudy, Rennes (FR); Olivier Busnel, Fontenay (FR); Sylviane Muller, Strasbourg (FR)

(73) Assignee: Centre National de la Recherche Scientifique, Paris (FR)

( * ) Notice: Subject to any disclaimer, the term of this patent is extended or adjusted under 35 U.S.C. 154(b) by 2592 days.

(21) Appl. No.: 10/560,163

(22) PCT Filed: Jun. 11, 2004

(86) PCT No.: PCT/FR2004/001467
§ 371 (c)(1), (2), (4) Date: Sep. 27, 2010

(87) PCT Pub. No.: WO2004/111086
PCT Pub. Date: Dec. 23, 2004

(65) Prior Publication Data
US 2011/0044974 A1    Feb. 24, 2011

(30) Foreign Application Priority Data
Jun. 11, 2003 (FR) ...................................... 30 06992

(51) Int. Cl.
| | |
|---|---|
| C07K 7/08 | (2006.01) |
| C07K 16/00 | (2006.01) |
| C07K 16/42 | (2006.01) |
| A61K 39/00 | (2006.01) |
| A61K 38/10 | (2006.01) |
| A61P 31/04 | (2006.01) |
| A61K 39/395 | (2006.01) |

(52) U.S. Cl.
CPC ..................................... *A61K 39/395* (2013.01)

(58) Field of Classification Search
None
See application file for complete search history.

(56) References Cited

U.S. PATENT DOCUMENTS 2,097,533 A    12/1993 Lemaire
2003/0021797 A1   1/2003 Datta et al.

FOREIGN PATENT DOCUMENTS

| CA | 2097533 | 12/1993 |
|---|---|---|
| FR | 2 828 884 | 2/2003 |

OTHER PUBLICATIONS

Cheguillaume et al. Solution Synthesis and Characterization of Aza-beta3-peptides (Nr-Substituted Hydrazino Acetic Acid Oligomers) J. Org. Chem. 2001, 66, 4923-4929.*
Cheguillaume et al ("Solution Synthesis and Characterization of aza-B3-peptides (Nα-Substituted Hydrazino Acetic Acid Oligomers)" (Jun. 19, 2001) J. Org. Chem. 66: 4923-4929).*
Decker et al ("Identification of a Minimal T Cell Epitope Recognized by Antinucleosome Th Cells in the C-Terminal Region of Histone H4" (2000) The Journal of Immunology 165: 654-662).*
Merriam-Webster Dictionary, Medical definition of "derive", http://www.merriam-webster.com/medical/derive, downloaded on Sep. 28, 2013.*
WebMD, "Bacterial and Viral Infections" downloaded Sep. 28, 2013 from http://www.webmd.com/a-to-z-guides/bacterial-and-viral-infections.*
MedLine Plus, "T-cell count" downloaded on Sep. 28, 2013 from http://www.nlm.nih.gov/medlineplus/ency/article/003516.htm.*
Mayo Clinic, "Guillain-Barre syndrome" downloaded Aug. 28, 2013 from http://www.mayoclinic.com/health/guillain-barr-syndrome/DS00413.*
Decker P et al.: "Identification of a Minimal T Cell Epitope Recognized by Antinucleosome Th Cells in the C-Terminal Region of Histone H4" The Journal of Immunology, vol. 165, 2000, No. 2, pp. 654-662, XP002277566 the whole document.
Cheguillaume Arnaud et al: "Solution synthesis and characterization of aza-.beta.3-peptides (N.alpha.-substituted hydrazino acetic acid oligomers)" Journal of Organic Chemistry, American Chemical Society, Eaton, US, vol. 66, 2001, pp. 4923-4929. XP002197673 ISSN: 0022-3263 the whole document.
Bouget K et al: "Hydrazino-Aza and N-Azapeptoids With Therapeutic Potential As Anticancer Agents" Bioorganic & Medicinal Chemistry, Elsevier Science LTD, GB, vol. 11, No. 23, Nov. 17, 2003.,pp. 4881-4889, XP001187599 ISSN: 0968-0896 the whole doucment.

* cited by examiner

*Primary Examiner* — Jean Witz
*Assistant Examiner* — Mindy Newman
(74) *Attorney, Agent, or Firm* — Frommer Lawrence & Haug LLP; William S. Frommer

(57) ABSTRACT

The object of the present invention is analogues of peptides or parent proteins, these peptide analogues, comprising at least one aza-$\beta^3$ aminoacyl residue, and also their uses in pharmaceutical compositions or for the diagnosis of pathologies wherein the aforesaid peptides or parent proteins are involved.

19 Claims, 7 Drawing Sheets

Figure 1:
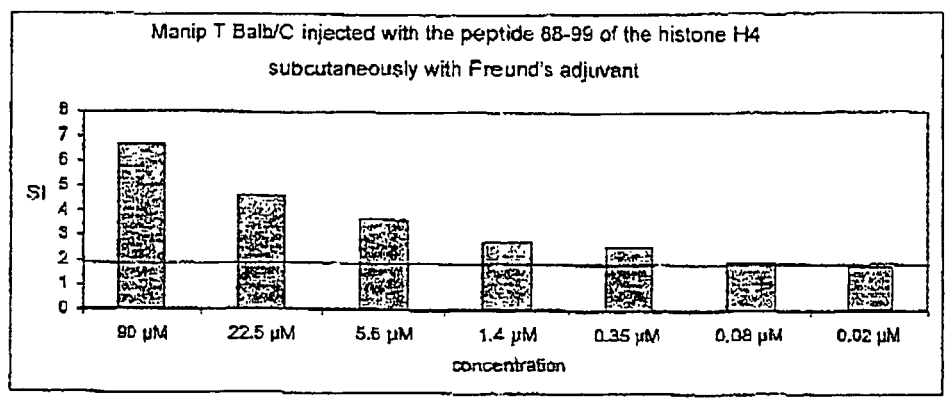
Figure 1:
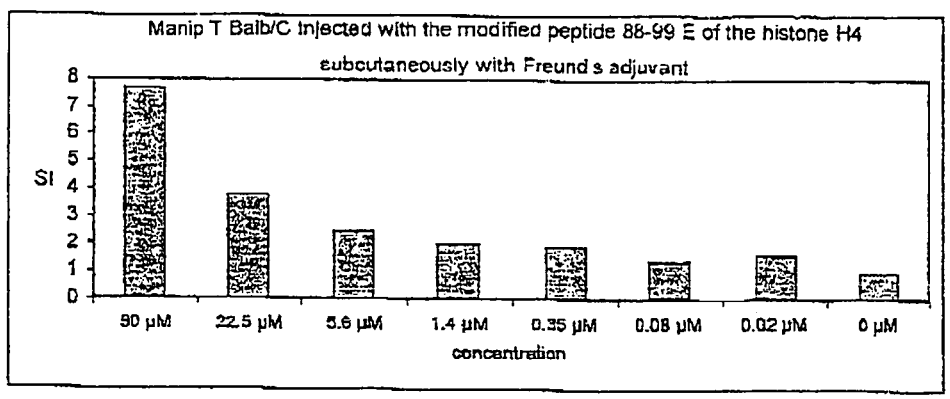

PEPTIDE ANALOGUES COMPRISING AT LEAST ONE TYPE OF AMINOACYLAZA-$G(B)<SP>3</SP>$ AND THE USE THEREOF, IN PARTICULAR FOR THERAPY

The object of the present invention is analogues of peptides or parent proteins, these peptide analogues, comprising at least one aza-$\beta^3$ aminoacyl residue, and their uses in pharmaceutical compositions or for the diagnosis of pathologies wherein the aforesaid peptides or parent proteins are involved.

The identification of the antigenic regions (or epitopes) recognised by the T cells and the understanding of the molecular and cellular bases of antigenic recognition are considered as key stages in the design and the development of vaccine and immunomodulation strategies. Immunisation by means of peptides corresponding to non-self (for example viral or bacterial) or self (for example tumoral) epitopes to induce antibodies and/or helper T lymphocytes (Th) or cytotoxic lymphocytes (CTL) specific for the tumour or the virus is nowadays a particularly promising strategy in the development of synthetic vaccines. In the case of antiviral vaccines for example, peptides present several major advantages over the standard preparations of attenuated or inactivated viruses, namely a simpler, chemically defined and perfectly controllable production process and better stability at ambient temperature. Therapeutic approaches based on the T $CD4^+$ epitopes of self antigens are also proposed.

In practice, however, the peptides are often found to be of low immunogenicity and do not make it possible to obtain high titres of antibodies capable of reacting with the natural protein or the viral particle. These limitations to the use of peptides in the development of synthetic vaccines are probably connected with substantial biodegradability in biological fluids, poor diffusion through the membrane systems and with the lack of selectivity towards the target.

Different approaches have been developed to "transform" the peptides into molecules capable of inducing a stronger and more specific humoral or cellular immune response. The introduction of pseudopeptide bonds into the antigenic peptides is one of the most interesting strategies for improving their intrinsic physical and chemical characteristics and their ability to interact with the immune system effectors. In spite of the important potential applications in the field of diagnosis, vaccination or immunomodulation, and the extent of the knowledge of these analogues acquired in the chemical and pharmacological fields, the pseudopeptides are still little used in immunology.

The purpose of the present invention is to provide peptide analogues resistant to degradation enzymes and capable of mimicking the activity of various natural peptides, vaccination agents or immunomodulation agents.

More particularly, the purpose of the invention is to provide peptide analogues which are characterized by the introduction of monomers not exhibiting carbon chiral centres, which makes it possible to overcome the difficulties associated with asymmetric synthesis and with the problems of epimerisation. This family of peptide analogues constitutes a new class of peptidomimetics, wherein the residues (side-chains) are carried by chiral nitrogen atoms of non-fixed configuration, which confers on them a great spatial adaptability. The correct positioning of the peptidomimetics constructed according to this principle in an enzymatic site occurs by the simultaneous displacement of conformational and configurational equilibria. The action of such a compound, from the stereochemical point of view, is equivalent to that of a mixture of diastereoisomers in rapid equilibrium, the interaction with the enzymatic site displacing the equilibrium towards the stereoisomer or stereoisomers with the greatest affinity. Other potential benefits can also result from this, such as, from a chemical point of view, a simplification of the methods of synthesis (elimination of stereochemical problems) and, besides, a greater resistance of such analogues of modified skeleton to the action of peptidases. The prior synthesis of these monomers allows the introduction of a good variety of side-chains, both in the proteogenic and the non-proteogenic series, and hence makes it possible to modify to a certain degree their affinity and their lipophily.

Also a purpose of the invention is to provide pharmaceutical compositions containing such peptide analogues, and methods for in vitro diagnosis of pathologies involving the parent peptides from which these peptide analogues are derived, and kits for the implementation of these methods.

The object of the present invention is the use of analogues of peptides or parent proteins, these peptide analogues, also called hybrid peptides, containing at least one aza-$\beta^3$-aminoacyl residue, namely:

a residue corresponding to the following formula (A) when it is situated in the N-terminal position,

wherein R represents H or a protective group of the amine function of the amino acids, such as Fmoc (fluorenylmethoxycarbonyl), Boc (tert-butoxycarbonyl), or Z (benzyloxycarbonyl), and $R_1$ represents a side-chain selected from those of the amino acids, a residue corresponding to the following formula (B) when it is situated in the C-terminal position,

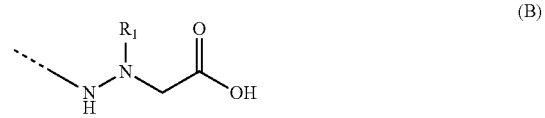

wherein $R_1$ represents a side-chain selected from those of the amino acids, a residue corresponding to the following formula (C) when it is situated in the chain of the said hybrid peptides,

wherein $R_1$ represents a side-chain selected from those of the amino acids, for the preparation:
of a vaccine or of a medicament intended for the prevention or for the treatment of pathologies associated with the presence, in the body of an individual, of an exogenous or endogenous protein capable of being directly or indirectly involved in the process of appearance and/or development of those pathologies, or of a vaccine or of a medicament intended for the prevention or for the treatment of pathologies involving the molecules of the major histocompatibility complex and/or the T cell receptors, or of a vaccine or of a medicament intended for the prevention or for the treatment of pathologies associated with the presence in the body of an individual of an antibody capable of being recognised by an aforesaid hybrid peptide, or for the implementation of a method for the in vitro diagnosis of the aforesaid pathologies.

The aforesaid hybrid peptides of the invention can also be defined by the following general formula (A):

AA1-(AA2- ... -AAn-1)-AAn    (A)

wherein:
AA1 to AAn represent:
an amino acid corresponding to an aminoacyl residue situated in the same position in the peptide or the parent protein from which the hybrid peptides are derived,
or an aza-$\beta^3$ aminoacyl monomer residue analogous to the aminoacyl residue initially present at the same position in the peptide or the parent protein from which the hybrid peptides are derived, the said aza-$\beta^3$ aminoacyl monomer corresponding to the formulae (A), (B), or (C) stated above, depending on whether it is respectively in the N-terminal or C-terminal position, or in the chain of the said hybrid peptides, and wherein $R_1$ is identical to the side-chain of the initial amino acid of the peptide or of the parent protein to which the said aza-$\beta^3$ aminoacyl monomer corresponds,
and n represents a whole number from 4 to about 100.

More particularly, the object of the present invention is the use of hybrid peptides such as defined above for the preparation of a vaccine or of a medicament intended for the prevention or the treatment of pathologies of viral or bacterial origin, or of autoimmune pathologies, or of neurodegenerative diseases.

More particularly, the present invention also concerns the aforesaid use of hybrid peptides such as defined above, wherein the pathologies are selected from:
pathologies involving molecules of the major histocompatibility complex and/or the T cell receptors,
autoimmune diseases, and in particular Hashimoto thyroiditis, Basedow's disease, Addison's disease, pituitary insufficiency, Biermer's gastritis, certain forms of sterility, type 1 juvenile diabetes, Goodpasture's syndrome, myasthenia, acute articular rheumatism, pemphigus, bullous pemphigoid, herpetiform dermatitis, vitiligo, alopecia, psoriasis, sympathetic ophthalmia, uveitis, Guillain-Baré's syndrome, multiple sclerosis, haemolytic anaemia, idiopathic thrombocytopaenic purpura, idiopathic leucopaenia, primary biliary cirrhosis, active chronic hepatitis, ulcerative colitis, Crohn's ileitis, Gougerot-Sjögren syndrome, rheumatoid polyarthritis, dermatopolymyositis, scleroderma, mixed connective tissue disease, discoid lupus erythematosus and systemic lupus erythematosus.
neurodegenerative diseases,
diseases of viral origin, in particular:
AIDS caused by human immunodeficiency virus HIV-1 and HIV-2,
paraplegia associated with HTVL-1, or adult T cell leukaemia, caused by human T cell leukaemia virus (HTLV virus),
infections caused by the syncytial respiratory virus,
infections caused by the Coxsackie virus, for example acute lymphocytic meningitis,
infections caused by the Epstein-Barr virus, for example infectious mononucleosis,
infections caused by the cytomegalovirus, for example cytomegalic inclusion disease,
herpes caused by the human herpes virus,
herpes caused by herpes simplex virus 6,
infections caused by the human parvovirus B19, for example infectious gastroenteritis,
hepatitis B caused by the hepatitis B virus,
hepatitis C caused by the hepatitis C virus,
influenza caused by the influenza virus,
rubella caused by the rubella virus, infections caused by the Dengue virus, for example the arboviroses,
colds, rhinitis and coryza caused by the rhinoviruses,
aphthous fever caused by aphthous fever virus,
certain cancers linked with viruses, such as the papilloma viruses.

More particularly, an object of the invention is the aforesaid use of hybrid peptides of the following formula (I):

$$aa_l\text{-}N^\alpha haa_m\text{-}aa_n\text{-}N^\alpha haa_o\text{-}aa_p \quad\quad (I)$$

wherein:
$aa_l$, $aa_n$ and $aa_p$ represent an aminoacyl residue, or a concatenation of aminoacyl residues, corresponding to the aminoacyl residues present at the same positions in the peptide or the parent protein from which the hybrid peptides are derived,
$N^\alpha haa_m$ and $N^\alpha haa_o$ represent a monomeric aza-$\beta^3$ aminoacyl residue, or a concatenation of monomeric aza-$\beta^3$ aminoacyl residues analogous to the aminoacyl residues initially present at the same position in the peptide or the parent protein from which the hybrid peptides are derived, the said aza-$\beta^3$ aminoacyl monomers corresponding to the formulae (A), (B) or (C) shown above, depending on whether they are respectively in the N-terminal or C-terminal position, or in the chain of the said hybrid peptides, and wherein $R_1$ is identical to the side-chain of the initial amino acid of the peptide or of the parent protein to which the said aza-$\beta^3$ aminoacyl monomers correspond,
l, m, n, o, and p represent zero, or a whole number lying between 1 and 20, provided that at least one of m or o is different from zero, and that the minimum number of residues in the said hybrid peptides of formula (I) is 4.

More particularly, the invention concerns the aforesaid use of hybrid peptides derived from the epitope 88-99 of the histone H4 as the parent peptide, and corresponding to SEQ ID NO: 1, at least one of whose initial amino acids is replaced by an analogous aza-$\beta^3$ amino acid residue, for the preparation of a medicament, or vaccine, intended for the prevention or for the treatment of systemic lupus erythematosus.

As such, the invention more particularly concerns the aforesaid use of hybrid peptides derived from the epitope 88-99 defined above, and having the following formulae:

SEQ ID NO: 2 (or peptide E):
$^{88}$H$_2$N-Tyr-Ala-Leu-Lys-Arg-Gln-Gly-Arg-Thr-N$\alpha$-hLeu-Tyr-Gly-OH$^{99}$ SEQ ID NO: 3 (or peptide C):
$^{88}$H$_2$N-Tyr-Ala-N$\alpha$-hLeu-Lys-Arg-Gln-Gly-Arg-Thr-Leu-Tyr-Gly-OH$^{99}$ SEQ ID NO: 4 (or peptide A):
$^{88}$H$_2$N-Tyr-N$\alpha$-hAla-Leu-Lys-Arg-Gln-Gly-Arg-Thr-Leu-Tyr-Gly-OH$^{99}$ -continued SEQ ID NO: 5 (or peptide B):
$^{88}$H$_2$N-Tyr-Nα-hAla-Nα-hLeu-Lys-Arg-Gln-Gly-Arg-Thr-Leu-Tyr-Gly-OH$^{99}$ SEQ ID NO: 6 (or peptide D):
$^{88}$H$_2$N-Tyr-Ala-Leu-Nα-hLys-Arg-Gln-Gly-Arg-Thr-Leu-Tyr-Gly-OH$^{99}$ SEQ ID NO: 7 (or peptide G):
$^{88}$H$_2$N-Tyr-Ala-Leu-Lys-Arg-Gln-Gly-Arg-Thr-Nα-hLeu-Nα-hTyr-Gly-OH$^{99}$ SEQ ID NO: 8:
$^{88}$H$_2$N-Tyr-Ala-Leu-Lys-Arg-Gln-Nα-hGly-Arg-Thr-Leu-Tyr-Gly-OH$^{99}$ SEQ ID NO: 9:
$^{88}$H$_2$N-Tyr-Ala-Leu-Lys-Arg-Gln-Gly-Nα-hArg-Thr-Leu-Tyr-Gly-OH$^{99}$ SEQ ID NO: 10:
$^{88}$H$_2$N-Tyr-Ala-Leu-Lys-Nα-hArg-Gln-Gly-Arg-Thr-Leu-Tyr-Gly-OH$^{99}$ SEQ ID NO: 11:
$^{88}$H$_2$N-Tyr-Ala-Leu-Lys-Arg-Gln-Gly-Arg-Thr-Leu-Nα-hTyr-Gly-OH$^{99}$ SEQ ID NO: 12 (or peptide F):
$^{88}$H$_2$N-Nα-hTyr-Ala-Leu-Lys-Arg-Gln-Gly-Arg-Thr-Leu-Tyr-Gly-OH$^{99}$ SEQ ID NO: 13 (or peptide H):
$^{88}$H$_2$N-Tyr-Ala-Leu-Lys-Arg-Gln-Gly-Arg-Thr-Leu-Tyr-Nα-hGly-OH$^{99}$ SEQ ID NO: 14 (or peptide I):
$^{88}$H$_2$N-Tyr-Ala-Leu-Lys-Arg-Gln-Gly-Arg-Thr-N$^α$-hLeu-Nα-hTyr-Nα-hGly-OH$^{99}$ More particularly, the invention concerns the aforesaid use of the hybrid peptide of formula SEQ ID NO: 2.

More particularly, the invention concerns the aforesaid use of the hybrid peptide of formula SEQ ID NO: 7.

More particularly, the invention concerns the aforesaid use of hybrid peptides derived from the peptide 307-319 of the haemagglutinin of influenza virus as the parent peptide, and corresponding to SEQ ID NO: 15, one at least of whose initial amino acids is replaced by an analogous aza-β$^3$ amino acid residue, for the preparation of a medicament, or vaccine, intended for the prevention or for the treatment of influenza or of any other pathology such as listed above and for which a molecule containing a B or CTL (CD8) epitope is administered in combination with the sequence 307-319 HA which contains a so-called universal T CD4 epitope.

As such, more particularly, the invention concerns the aforesaid use of hybrid peptides having the following formulae:

SEQ ID NO: 16 (or peptide A'):
$^{307}$H$_2$N-Nα-hPro-Lys-Tyr-Val-Lys-Gln-Asn-Thr-Leu-Lys-Leu-Ala-Thr-OH$^{319}$ SEQ ID NO: 17 (or peptide B'):
$^{307}$H$_2$N-Pro-Nα-hLys-Tyr-Val-Lys-Gln-Asn-Thr-Leu-Lys-Leu-Ala-Thr-OH$^{319}$ SEQ ID NO: 18 (or peptide C'):
$^{307}$H$_2$N-Pro-Lys-Nα-hTyr-Val-Lys-Gln-Asn-Thr-Leu-Lys-Leu-Ala-Thr-OH$^{319}$ SEQ ID NO: 19 (or peptide D'):
$^{307}$H$_2$N-Pro-Lys-Tyr-Nα-hVal-Lys-Gln-Asn-Thr-Leu-Lys-Leu-Ala-Thr-OH$^{319}$ SEQ ID NO: 20 (or peptide E'):
$^{307}$H$_2$N-Pro-Lys-Tyr-Val-Nα-hLys-Gln-Asn-Thr-Leu-Lys-Leu-Ala-Thr-OH$^{319}$ SEQ ID NO: 21 (or peptide F'):
$^{307}$H$_2$N-Pro-Lys-Tyr-Val-Lys-Gln-Asn-Thr-Nα-hLeu-Lys-Leu-Ala-Thr-OH$^{319}$ SEQ ID NO: 22 (or peptide G'):
$^{307}$H$_2$N-Pro-Lys-Tyr-Val-Lys-Gln-Asn-Thr-Leu-Nα-hLys-Leu-Ala-Thr-OH$^{319}$ SEQ ID NO: 23 (or peptide H'):
$^{307}$H$_2$N-Pro-Lys-Tyr-Val-Lys-Gln-Nα-hAsn-Thr-Leu-Lys-Leu-Ala-Thr-OH$^{319}$ SEQ ID NO: 24 (or peptide I'):
$^{307}$H$_2$N-Pro-Lys-Tyr-Val-Lys-Gln-Asn-Thr-Leu-Lys-Nα-hLeu-Ala-Thr-OH$^{319}$ SEQ ID NO: 25 (or peptide J'):
$^{307}$H$_2$N-Pro-Lys-Tyr-Val-Lys-Gln-Asn-Thr-Leu-Lys-Leu-Nα-hAla-Thr-OH$^{319}$ SEQ ID NO: 26 (or peptide K'):
$^{307}$H$_2$N-Pro-Lys-Tyr-Val-Lys-Gln-Asn-Thr-Leu-Nα-hLys-Nα-hLeu-Nα-hAla-Thr-OH$^{319}$ SEQ ID NO: 27 (or peptide L'):
$^{307}$H$_2$N-Pro-Lys-Tyr-Val-Lys-Gln-Asn-Thr-Leu-Lys-Nα-hLeu-Nα-hAla-Thr-OH$^{319}$ More particularly, the invention concerns the aforesaid use of the hybrid peptide of formula SEQ ID NO: 25.

Also an object of the invention are hybrid peptides containing at least one aza-$\beta^3$ amino acid, these hybrid peptides being analogues of peptides or parent proteins, the said hybrid peptides containing at least one initial amino acid of the peptide or of the parent protein.

More particularly, the invention concerns hybrid peptides such as defined above, and corresponding to the following general formula (A):

AA1-(AA2-...-AAn-1)-AAn    (A)

wherein:
AA1 to AAn represent:
  an amino acid corresponding to an aminoacyl residue situated at the same position in the peptide or the parent protein from which the hybrid peptides are derived,
  or an aza-$\beta^3$ aminoacyl monomer residue analogous to the aminoacyl residue initially present at the same position in the peptide or the parent protein from which the hybrid peptides are derived, the said aza-$\beta^3$ aminoacyl monomer corresponding to the formulae (A), (B) or (C) stated above, depending on whether it is respectively in the N-terminal or C-terminal position, or in the chain of the said hybrid peptides, and wherein $R_1$ is identical to the side-chain of the initial amino acid of the peptide or of the parent protein to which the said aza-$\beta^3$ aminoacyl monomer corresponds,
  one at least of AA1 to AAn representing an amino acid of the parent peptide, namely an aminoacyl residue situated at the same position in the peptide or the parent protein from which the hybrid peptides are derived,
and n represents a whole number from 4 to about 100.

As such, the invention more particularly concerns the hybrid peptides defined above of the following formula (I):

$$aa_l\text{-}N^\alpha haa_m\text{-}aa_n\text{-}N^\alpha haa_o\text{-}aa_p \qquad (I)$$

wherein:
$aa_l$, $aa_n$ and $aa_p$ represent an aminoacyl residue, or a concatenation of aminoacyl residues, corresponding to the aminoacyl residues present at the same positions in the peptide or the parent protein from which the hybrid peptides are derived, $N^\alpha haa_m$ and $N^\alpha haa_o$ represent a monomeric aza-$\beta^3$ aminoacyl residue, or a concatenation of monomeric aza-$\beta^3$ aminoacyl residues, analogous to the aminoacyl residues initially present at the same position in the peptide or the parent protein from which the hybrid peptides are derived, the said aza-$\beta^3$ aminoacyl monomers corresponding to the formulae (A), (B), or (C) mentioned above, depending on whether they are respectively in the N-terminal position, C-terminal position, or in the chain of the said hybrid peptides, and wherein $R_1$ is identical to the side-chain of the initial amino acid of the peptide or of the parent protein to which the said aza-$\beta^3$ aminoacyl monomers correspond, l, m, n, o, and p represent zero, or a whole number lying between 1 and 20, providing that at least one of m or o is different from zero, that the minimum number of residues in the said hybrid peptides of formula (I) is 4, and at least one of l, n, or p is different from zero.

More particularly, an object of the invention is the aforesaid hybrid peptides of the following formulae:

```
SEQ ID NO: 2 (or peptide E):
88H2N-Tyr-Ala-Leu-Lys-Arg-Gln-Gly-Arg-Thr-Nα-hLeu-Tyr-Gly-OH99

SEQ ID NO: 3 (or peptide C):
88H2N-Tyr-Ala-Nα-hLeu-Lys-Arg-Gln-Gly-Arg-Thr-Leu-Tyr-Gly-OH99

SEQ ID NO: 4 (or peptide A):
88H2N-Tyr-Nα-hAla-Leu-Lys-Arg-Gln-Gly-Arg-Thr-Leu-Tyr-Gly-OH99

SEQ ID NO: 5 (or peptide B):
88H2N-Tyr-Nα-hAla-Nα-hLeu-Lys-Arg-Gln-Gly-Arg-Thr-Leu-Tyr-Gly-OH99

SEQ ID NO: 6 (or peptide D):
88H2N-Tyr-Ala-Leu-Nα-hLys-Arg-Gln-Gly-Arg-Thr-Leu-Tyr-Gly-OH99

SEQ ID NO: 7 (or peptide G):
88H2N-Tyr-Ala-Leu-Lys-Arg-Gln-Gly-Arg-Thr-Nα-hLeu-Nα-hTyr-Gly-OH99

SEQ ID NO: 8:
88H2N-Tyr-Ala-Leu-Lys-Arg-Gln-Nα-hGly-Arg-Thr-Leu-Tyr-Gly-OH99

SEQ ID NO: 9:
88H2N-Tyr-Ala-Leu-Lys-Arg-Gln-Gly-Nα-hArg-Thr-Leu-Tyr-Gly-OH99

SEQ ID NO: 10:
88H2N-Tyr-Ala-Leu-Lys-Nα-hArg-Gln-Gly-Arg-Thr-Leu-Tyr-Gly-OH99

SEQ ID NO: 11:
88H2N-Tyr-Ala-Leu-Lys-Arg-Gln-Gly-Arg-Thr-Leu-Nα-hTyr-Gly-OH99

SEQ ID NO: 12 (or peptide F):
88H2N-Nα-hTyr-Ala-Leu-Lys-Arg-Gln-Gly-Arg-Thr-Leu-Tyr-Gly-OH99

SEQ ID NO: 13 (or peptide H):
88H2N-Tyr-Ala-Leu-Lys-Arg-Gln-Gly-Arg-Thr-Leu-Tyr-Nα-hGly-OH99

SEQ ID NO: 14 (or peptide I):
88H2N-Tyr-Ala-Leu-Lys-Arg-Gln-Gly-Arg-Thr-Nα-hLeu-Nα-hTyr-Nα-hGly-OH99
```

-continued

SEQ ID NO: 16 (or peptide A'):
[307]H₂N-Nα-hPro-Lys-Tyr-Val-Lys-Gln-Asn-Thr-Leu-Lys-Leu-Ala-Thr-OH[319]

SEQ ID NO: 17 (or peptide B'):
[307]H₂N-Pro-Nα-hLys-Tyr-Val-Lys-Gln-Asn-Thr-Leu-Lys-Leu-Ala-Thr-OH[319]

SEQ ID NO: 18 (or peptide C'):
[307]H₂N-Pro-Lys-Nα-hTyr-Val-Lys-Gln-Asn-Thr-Leu-Lys-Leu-Ala-Thr-OH[319]

SEQ ID NO: 19 (or peptide D'):
[307]H₂N-Pro-Lys-Tyr-Nα-hVal-Lys-Gln-Asn-Thr-Leu-Lys-Leu-Ala-Thr-OH[319]

SEQ ID NO: 20 (or peptide E'):
[307]H₂N-Pro-Lys-Tyr-Val-Nα-hLys-Gln-Asn-Thr-Leu-Lys-Leu-Ala-Thr-OH[319]

SEQ ID NO: 21 (or peptide F'):
[307]H₂N-Pro-Lys-Tyr-Val-Lys-Gln-Asn-Thr-Nα-hLeu-Lys-Leu-Ala-Thr-OH[319]

SEQ ID NO: 22 (or peptide G'):
[307]H₂N-Pro-Lys-Tyr-Val-Lys-Gln-Asn-Thr-Leu-Nα-hLys-Leu-Ala-Thr-OH[319]

SEQ ID NO: 23 (or peptide H'):
[307]H₂N-Pro-Lys-Tyr-Val-Lys-Gln-Nα-hAsn-Thr-Leu-Lys-Leu-Ala-Thr-OH[319]

SEQ ID NO: 24 (or peptide I'):
[307]H₂N-Pro-Lys-Tyr-Val-Lys-Gln-Asn-Thr-Leu-Lys-Nα-hLeu-Ala-Thr-OH[319]

SEQ ID NO: 25 (or peptide J'):
[307]H₂N-Pro-Lys-Tyr-Val-Lys-Gln-Asn-Thr-Leu-Lys-Leu-Nα-hAla-Thr-OH[319]

SEQ ID NO: 26 (or peptide K'):
[307]H₂N-Pro-Lys-Tyr-Val-Lys-Gln-Asn-Thr-Leu-Nα-hLys-Nα-hLeu-Nα-hAla-Thr-OH[319]

SEQ ID NO: 27 (or peptide L'):
[307]H₂N-Pro-Lys-Tyr-Val-Lys-Gln-Asn-Thr-Leu-Lys-Nα-hLeu-Nα-hAla-Thr-OH[319]

Still more particularly, the invention concerns the hybrid peptides such as defined above of the following formula:

SEQ ID NO: 2 (or peptide E):
[88]H₂N-Tyr-Ala-Leu-Lys-Arg-Gln-Gly-Arg-Thr-Nα-hLeu-Tyr-Gly-OH[99]

SEQ ID NO: 7 (or peptide G):
[88]H₂N-Tyr-Ala-Leu-Lys-Arg-Gln-Gly-Arg-Thr-Nα-hLeu-Nα-hTyr-Gly-OH[99]

SEQ ID NO: 25 (or peptide J'):
[307]H₂N-Pro-Lys-Tyr-Val-Lys-Gln-Asn-Thr-Leu-Lys-Leu-Nα-hAla-Thr-OH[319]

The invention also concerns a process for preparation of aza-β³ amino acids characterised in that it includes a stage of treatment of the substituted and protected hydrazine of the following formula (D):

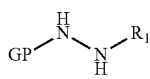

(D)

wherein R represents a side-chain selected from those of the amino acids, if necessary protected, and GP a protective group of amine functional groups, such as Boc, Fmoc, or Z, with glyoxylic acid with stirring in the presence of NaBH₃CN in an acidic medium, which leads in one stage to the aza-β³ amino acid compound of formula

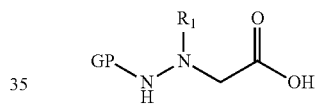

wherein R and GP are as defined above, and the said compound can if necessary be deprotected, in particular by means of HCl, of piperidine, or of palladiated hydrogen, in order to remove the group GP (Boc, Fmoc, or Z) and replace it with H.

More particularly, the invention concerns the following aza-β³ amino acids:

Fmoc aza-β³-Glycine (Fmoc-NαhGly-OH),
Fmoc aza-β³-Alanine (Fmoc-NαhAla-OH),
Fmoc aza-β³-Leucine (Fmoc-NαhLeu-OH),
Fmoc aza-β³-Valine (Fmoc-NαhVal-OH),
Fmoc aza-β³-Lysine (Fmoc-NαLys(Boc)-OH),
Fmoc aza-β³-Aspartic acid (Fmoc-NαhAsp(OtBu)-OH),
Fmoc aza-β³-Methionine (Fmoc-NβhMet-OH),
Fmoc aza-β³ Arginine (Fmoc-NαhArg (Boc)-OH),
Fmoc aza-β³-Tyrosine (Fmoc-NβhTyr(OCH₂OEt)-OH)
Fmoc aza-β³-Asn (Fmoc-NαhAsn(Trt)-OH).
Fmoc aza-β³-Pro (Fmoc-NαhPro-OH).
the formulae whereof are respectively as follows:

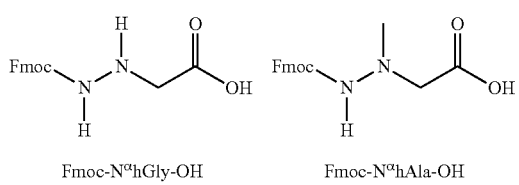

Fmoc-NαhGly-OH    Fmoc-NαhAla-OH

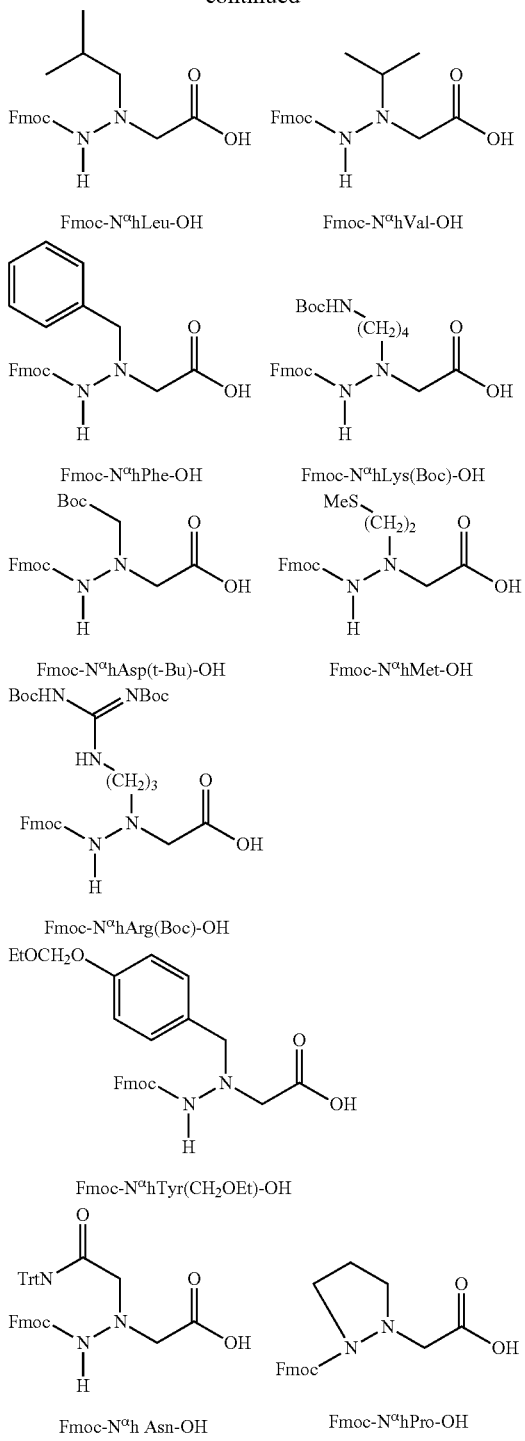

The invention also concerns complexes between a hybrid peptide such as defined above, and a component of the major histocompatibility complex (also referred to as MHC-hybrid complex), and possibly a T cell receptor (also referred to as MHC-hybrid-T receptor complex).

More particularly, the invention concerns a complex between a hybrid peptide such as defined above, and a T cell receptor.

Also an object of the invention is a method for in vitro diagnosis of pathologies associated with the presence in the body of a patient of an exogenous or endogenous protein capable of being directly or indirectly involved in the process of appearance and/or of development of those pathologies, characterized in that it comprises:

contacting a biological sample deriving from a patient capable of being a carrier of antibodies directed against the said protein, with a hybrid peptide such as defined above, the said hybrid peptide being derived from all or part of the said endogenous or exogenous protein, or derived from a peptide capable of being recognized by antibodies themselves recognizing the exogenous or endogenous protein, under conditions allowing the reaction between the antibodies directed against the protein and capable of being present in the biological sample, and the aforesaid hybrid peptide;

the in vitro detection of the antigen/antibody complex capable of being formed in the preceding stage or the in vitro detection of antibodies circulating in the patient by a competitive test using an anti-hybrid antibody.

Also an object of the invention is an outfit or kit for the implementation of an in vitro diagnostic method such as defined above, comprising:

a hybrid peptide derived from all or part of the endogenous or exogenous protein, or corresponding to a peptide capable of being recognised by antibodies themselves recognising the exogenous or endogenous protein, reagents for rendering a medium suitable for the development of an immunological reaction, reagents making it possible to detect the antigen/antibody complex which has been produced as a result of the immunological reaction, the said reagents possibly containing a marker or being capable of being recognised in their turn by a labelled reagent, more particularly in the case where the hybrid peptide or the aforesaid anti-hybrid antibodies are not labelled.

The invention also concerns pharmaceutical compositions, in particular vaccines, containing at least one hybrid peptide such as defined above, whether or not in combination with a physiologically acceptable vehicle.

More particularly, an object of the invention are the aforesaid pharmaceutical compositions containing at least one hybrid peptide such as defined above, whether or not associated with a proteic or non-proteic carrier molecule, capable of inducing in vivo the production of antibodies neutralizing the exogenous or endogenous protein responsible for the pathology, or inducing in vivo a cytotoxic or helper cellular immune response.

The invention also concerns polyclonal or monoclonal anti-hybrid peptides antibodies such as obtained by immunization of an animal with at least one hybrid peptide defined above, the said antibodies being capable of forming a complex with these hybrid peptides, and/or with the peptides or parent proteins corresponding to these latter, and characterized in that they recognize the parent peptide or the parent protein with an affinity at least equal to that displayed by the anti-parent peptide or anti-parent protein antibodies towards the parent peptide or the parent protein.

More particularly, an object of the invention is anti-idiotype antibodies capable of forming a complex with the aforesaid antibodies, such as obtained by immunization of an animal with the said antibodies.

The invention also concerns an in vitro method for diagnosis of pathologies associated with the presence in the body of a patient of an exogenous or endogenous protein capable of being directly or indirectly involved in the process of appearance and/or development of these pathologies, the said method being characterized in that it comprises:

contacting a biological sample deriving from a patient capable of being a carrier of the said protein, with at least one of the aforesaid antibodies, the antibodies being advantageously directed against a hybrid peptide derived from all or part of the said endogenous or exogenous protein, or under conditions allowing the reaction between the protein capable of being present in the biological sample, and the aforesaid antibodies directed against the aforesaid hybrid peptide;

the in vitro detection of the antigen/antibody complex capable of being formed in the preceding stage.

Also an object of the invention is an outfit or kit for the implementation of an in vitro diagnostic method such as defined above, comprising:

aforesaid antibodies, directed against that hybrid peptide;
reagents to render a medium suitable for the development of an immunological reaction;
reagents making it possible to detect the antigen/antibody complex which has been produced as a result of the immunological reaction, the said reagents possibly containing a marker or being capable of being recognized in their turn by a labeled reagent, more particularly in the case where the hybrid peptide or the aforesaid anti-hybrid antibodies are not labeled.

The invention also concerns pharmaceutical compositions, in particular vaccines, containing at least one aforesaid anti-idiotype, in combination with a physiologically acceptable vehicle.

More particularly, an object of the invention are the aforesaid pharmaceutical compositions containing at least one anti-idiotype such as defined above, combined with a proteic or non-proteic carrier molecule, capable of inducing in vivo the production of antibodies neutralizing the exogenous or endogenous protein responsible for the pathology, or inducing in vivo a cytotoxic cellular immune response.

The invention also concerns pharmaceutical compositions, containing antibodies such as defined above, whether or not in combination with a physiologically acceptable vehicle.

The invention will be further illustrated by means of the detailed description that follows of the synthesis of aza-$\beta^3$ amino acids, and of hybrid peptides containing them, and of their biological activity.

I) Hybrid Peptides of the Histone H4

The sequence on which the inventors worked during an initial period is a peptide from the histone H4 (residues 88-99: YALKRQGRTLYG) which represents a minimum immunodominant T CD4+ epitope recognized by ganglial Th cells of mice immunized against nucleosome, the basic structure of chromatin, made up of DNA and the four histones H2A, H2B, H3 and H4. In recent years, it has been demonstrated that the nucleosome plays a fundamental role as antigen and immunogen in a systemic autoimmune disease, systemic lupus erythematosus, which affects 1 million Americans today. This peptide of the C-terminal region of the histone H4 has the important property of not being recognised by Th cells generated against the isolated H4 protein, but only by Th cells generated against the nucleosome. Detailed studies of this peptide in the normal BALB/c mouse and by means of a murine lupus model (NZBxNZW mouse) have made it possible to obtain information concerning the T CD4+ and B (production of antibodies) cellular response directed against this peptide.

The synthesis of several analogues of this peptide 88-99 of the histone H4 was performed by successively replacing different positions by their respective N$^\alpha$haa analogue, according to the methodology described below.

A) Synthesis Methodology

The synthesis described below is that of aza-$\beta^3$ peptides or hybrid peptides including one or several aza-$\beta^3$ amino acid monomers, nitrogen analogues of amino acids. The side-chains of the monomers mimicking the amino acids are borne by nitrogen atoms which are isoelectronic to the CH$\alpha$, (chiral nitrogen atoms of non-fixed configuration), which confers on them great conformational freedom. Moreover, these monomers do not have any centre of asymmetry of fixed configuration. The correct positioning of the peptide chain in an enzymatic site occurs by the simultaneous displacement of conformational and configurational equilibria. The action of such a compound, from a stereochemical point of view, is equivalent to that of a mixture of diastereoisomers in rapid equilibrium, the interaction with the enzymatic site displacing the equilibrium towards that with the highest affinity.

The method of the present invention makes it possible to introduce a great variety of side-chains, proteogenic or non-proteogenic, in selected positions. Other potential benefits also result from this, such as a simplification of the methods of synthesis (elimination of stereochemical problems) and greater resistance of such analogues of modified skeleton to the action of peptidases. This makes it possible on the one hand to mimic the majority of natural and unnatural amino acids and on the other hand to introduce into the pseudopeptide skeleton side-chains capable of modulating its biophysical characteristics. The introduction of groups favouring the passage of these analogues across the cell membranes (lipophilic chains) or increasing their solubility in the plasma medium (perfluorinated groups for example) allows us to modify, or indeed to optimize, the bioavailability of these compounds.

a) Aza-$\beta^3$-Amino Acid Monomers

Two synthesis methodologies are used to obtain the aza-$\beta^3$-amino acid monomers from appropriately substituted and protected hydrazines, depending on the nature of the side-chains which it is desired to mimic Either by bromoacetylation of N,N'-disubstituted hydrazines, the deprotection of the orthogonally protected monomer leading to the desired aza $\beta^3$ amino acid with yields of the order of 60-80%.

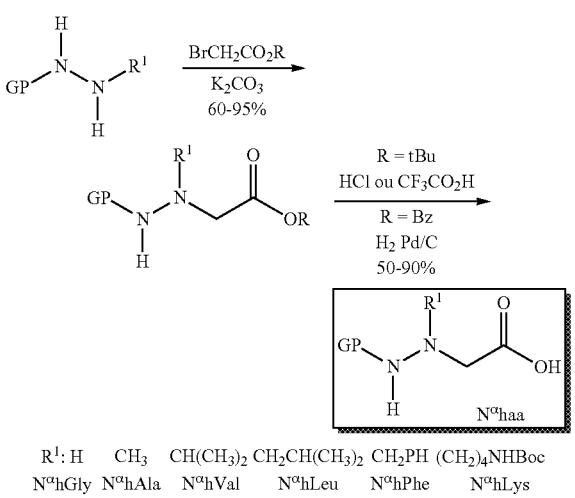

| R$^1$: | H | CH$_3$ | CH(CH$_3$)$_2$ | CH$_2$CH(CH$_3$)$_2$ | CH$_2$PH | (CH$_2$)$_4$NHBoc |
|---|---|---|---|---|---|---|
| | N$^\alpha$hGly | N$^\alpha$hAla | N$^\alpha$hVal | N$^\alpha$hLeu | N$^\alpha$hPhe | N$^\alpha$hLys |

This method consisting in effecting a nucleophilic substitution then a deprotection has been published in Synlett: New Monomers for Solid Phase Synthesis of Hydrazino-peptoids: the N$^\alpha$-Substituted-N$^\beta$-Protected hydrazinoglycines and N$^\alpha$-

Substituted-N$^\beta$-Protected hydrazinoglycinals. A. Cheguillaume, I. Doubli-Bounoua, M. Baudy-Floc'h, P. Le Grel, *Synlett* 2000, 3, 331-334.

Or by Reductive Amination of Glyoxylic Acid.

This method is a new method for synthesis of Fmoc-aza-$\beta^3$-amino acids (N$^\alpha$haa): glyoxylic acid (1.1 eq.) is added with stirring to a suspension of Fmoc protected substituted hydrazine (1 eq.) in 50 ml of EtOH. After 0.5 hrs, NaBH$_3$CN (1.2 eq.) is added to the mixture, the pH is adjusted to 3-4 by addition of 2N HCl, and after a further 0.5 hrs the pH is adjusted to 1. After 10 mins of stirring, the reaction mixture is concentrated by evaporation, then diluted by addition of 100 mL of ethyl acetate. The solution is washed successively with NaHCO$_3$ (5%) and brine, then, dried over Na$_2$SO$_4$. After evaporation of the solvent, the Fmoc-aza-$\beta^3$ amino acid monomer is obtained in yields of the order of 82-87%.

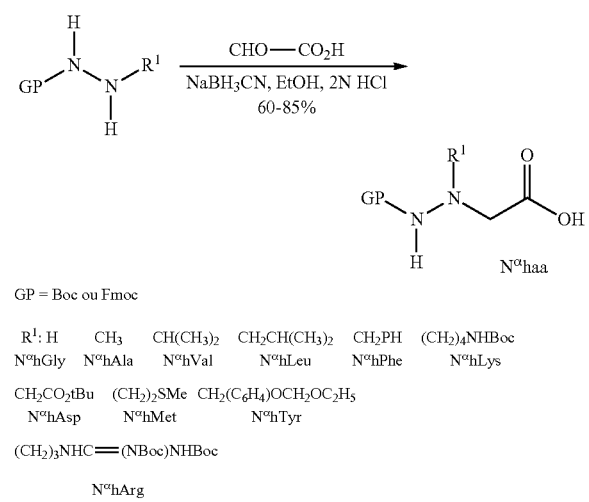

GP = Boc ou Fmoc

R$^1$: H    CH$_3$    CH(CH$_3$)$_2$    CH$_2$CH(CH$_3$)$_2$    CH$_2$PH    (CH$_2$)$_4$NHBoc
N$^\alpha$hGly  N$^\alpha$hAla  N$^\alpha$hVal        N$^\alpha$hLeu           N$^\alpha$hPhe    N$^\alpha$hLys CH$_2$CO$_2$tBu    (CH$_2$)$_2$SMe    CH$_2$(C$_6$H$_4$)OCH$_2$OC$_2$H$_5$
N$^\alpha$hAsp      N$^\alpha$hMet       N$^\alpha$hTyr (CH$_2$)$_3$NHC═(NBoc)NHBoc N$^\alpha$hArg a-1) Fmoc aza-$\beta^3$-Glycine (Fmoc-N$^\alpha$hGly-OH)

Glyoxylic acid (1.1 eq.) is added with stirring to a suspension of Fmoc carbazate (1 eq.) in 50 ml of EtOH. After 0.5 hrs, NaBH$_3$CN (1.2 eq.) is added to the mixture, the pH is adjusted to 3-4 by addition of 2N HCl and after a further 0.5 hrs the pH is adjusted to 1. After 10 mins of stirring, the reaction mixture is concentrated by evaporation, then diluted by addition of 100 mL of ethyl acetate. The solution is successively washed with NaHCO$_3$ (5%) and brine then dried over Na$_2$SO$_4$. After evaporation of the solvent, the Fmoc-aza-$\beta^3$ glycine monomer is obtained in a yield of 86%.

mp: 122-124° C. $^1$H NMR (DMSO): 3.75 (s, 2H, CH$_2$), 4.25 (t, 1H, J=6.8 Hz, CH), 4.50 (d, 2H, J=6.8 Hz, CH$_2$), 6.90 (br s, 1H, NH), 7.30-7.85 (m, 8H, Ar), 10.0 (s, 1H, OH). $^{13}$C NMR (DMSO): 162.90, 144.07, 141.59, 128.06, 127.38, 125.44, 120.30, 67.37, 58.00, 47.43. HRMS: (M+) Calc. for C$_{17}$H$_{15}$N$_2$O$_3$ 295.1082; Theor. 295.1083.

a-2) Fmoc-aza-$\beta^3$-Aspartic acid (Fmoc-N$^\alpha$hAsp(OtBu)-OH).

a-2-1) Fmoc NH—NHCH$_2$CO$_2$tBu:

A solution of 1.95 g of tert-butyl bromoacetate (10 mmol) in 10 ml of CH$_2$Cl$_2$ is added drop by drop with stirring at ambient temperature to a solution of 2.54 g of Fmoc carbazate (10 mmol) in 10 ml of DMF. After 12 hrs of stirring, the solvent is partially evaporated and the residue is purified by chromatography on silica gel (ethyl acetate/hexane 1/1) to obtain 2.79 g (yield: 76%) in the form of a colourless oil which crystallises slowly.

mp. 114-116° C. $^1$H NMR (CDCl$_3$) 1.50 (s, 9H, tBu), 3.61 (d, 2H, CH$_2$), 4.25 (t, 1H, J=6.8 Hz, CH), 4.44 (d, 2H, J=6.8 Hz, CH$_2$), 6.90 (brs, 1H, NH), 7.20-7.80 (m, 13H, ar). $^{13}$C NMR (CDCl$_3$): 171.55, 162.90, 144.07, 141.59, 128.06, 127.38, 125.44, 120.30, 82.21, 67.37, 53.10, 47.43, 28.42. C$_{21}$H$_{24}$N$_2$O$_4$ 368.1736 Calc: C, 68.45; H, 6.57; N, 7.61; Theor., C, 68.56; H, 6.73; N, 7.62.

a-2-2) Fmoc-N$^\alpha$hAsp(OtBu)-OH:

The monomer Fmoc-N$^\alpha$hAsp(OtBu) is prepared following the general procedure of reductive amination from the hydrazine Fmoc NH—NHCH$_2$CO$_2$tBu described above 87%; mp: 98-100° C. $^1$H NMR (CDCl$_3$): 1.50 (s, 9H, $^t$Bu), 3.60 (m, 2H, CH$_2$), 3.72 (m, 2H, CH$_2$), 4.22 (t, 1H, J=6.3 Hz, CH), 4.50 (d, 2H, J=6.3 Hz, CH$_2$), 7.20 (brs, 1H, NH), 7.22-7.84 (m, 8H, ar). $^{13}$C NMR (CDCl$_3$): 171.23, 171.00, 158.03, 143.61, 141.76, 128.33, 127.59, 125.33, 120.50, 83.80, 68.19, 59.20, 58.80, 47.49, 28.53. HRMS: (M+) Calc. for C$_{23}$H$_{26}$N$_2$O$_6$ 426.1790; Theor: 426.1790 Anal. calc: C, 64.76; H, 6.15; N, 6.57; Theor, C, 64.84; H, 6.18; N, 6.58.

a-3) Fmoc aza-$\beta^3$-Methionine (Fmoc-N$^\alpha$hMet-OH)

a-3-1) Fmoc NH—NH(CH$_2$)$_2$SMe:

16 ml of HCl (1%) is added to a solution of methyl thio acetaldehyde dimethyl acetal (5 g, 36 mmol) in CH$_2$Cl$_2$. After stirring at ambient temperature for 0.5 hrs, a suspension of Fmoc cabazate (8.38 g, 33 mmol) in 100 ml of THF is added. After 10 mins, 1 g of molecular sieve (4 Å) is added and the mixture is left with stirring for 12 hrs. 2.14 g of sodium cyanoborohydride (34 mmol) are then added in portions over a period of 45 mins, the pH being maintained at 3-4 by addition of a 2N solution of HCl. The mixture is stirred for a further 2 hrs, then adjusted to pH 1. The mixture is diluted in 50 ml of ethyl acetate, neutralized with NaHCO$_3$ and washed with brine. The aqueous phases are extracted with 3×50 ml of CH$_2$Cl$_2$. The organic phases are combined and dried over Na$_2$SO$_4$. The solvent is evaporated and the oil obtained is taken up into petroleum ether to give a precipitate of 4.54 g (42%).

mp:132° C. $^1$H NMR (CDCl$_3$): 2.15 (s, 3H, CH$_3$), 2.64 (t, 2H, J=Hz, CH$_2$), 3.12 (t, 2H, J=Hz, CH$_2$), 4.25 (t, 1H, J=6.6 Hz, CH), 4.52 (d, 2H, J=6.6 Hz, CH$_2$), 6.46 (brs, 1H, NH), 7.25-7.82 (m, 8H, ar), 8.21 (brs, 1H, NH). $^{13}$C NMR (CDCl$_3$): 157.67, 144.05, 141.75, 128.21, 127.51, 125.39, 120.46, 67.41, 50.09, 47.58, 32.63, 15.66. Anal calc. for C$_{18}$H$_{20}$O$_2$N$_2$S 328.1245: C, 65.83; H, 6.14; N, 8.54; S, 9.74. Theor: C, 65.90; H, 6.18; N, 8.62; S, 9.69.

a-3-2) Fmoc-N$^\alpha$hMet-OH:

The monomer Fmoc-N$^\alpha$hMet-OH is prepared following the general procedure of reductive amination from the hydrazine Fmoc NH—NH(CH$_2$)$_2$SMe described above 83%. $^1$H NMR (CDCl$_3$): 2.15 (s, 3H, CH$_3$), 2.55 (t, 2H, J=Hz, CH$_2$), 3.15 (t, 2H, J=Hz, CH$_2$), 3.69 (s, 2H, CH$_2$), 4.20 (t, 1H, J=6.6 Hz, CH), 4.50 (d, 2H, J=6.6 Hz, CH$_2$), 6.95 (brs, 1H, NH), 7.25-7.82 (m, 8H, ar), 9.24 (sl, 1H, OH). $^{13}$C NMR (CDCl$_3$): 173.42, 156.02, 143.87, 141.76, 128.26, 127.54, 125.38, 120.45, 67.54, 59.18, 56.70, 47.56, 30.12, 16.09. HRMS [M+H]$^+$ C$_{20}$H$_{23}$N$_2$O$_4$S Calc: 387.1379; Theor: 387.1379.

a-4) Fmoc aza-$\beta^3$-Tyrosine (Fmoc-N$^\alpha$hTyr(OCH$_2$OEt)-OH)

a-4-1) 4-(ethoxymethoxy)benzaldehyde:

A solution of chloromethyl ethyl ether (5.65 g, 0.06 mol) in 20 ml of THF at 0° C. is added to a mixture of 4-hydroxybenzaldehyde (5 g, 0.041 mol) and 12 ml of triethylamine in 30 ml of THF and the mixture is stirred at ambient temperature for 2 hrs. The triethylamine hydrochloride is filtered off and the solvent is evaporated under reduced pressure to give the 4-ethoxymethoxybenzaldehyde in the form of an oil (6.63 g, 90%).

$^1$H NMR (CDCl$_3$): 1.30 (t, 3H, J=7.1 Hz, CH$_3$), 3.70 (q, 2H, J=7.1 Hz, CH$_2$), 5.25 (s, 2H, CH$_2$), 7.15-7.80 (m, 4H, ar), 10.10 (s, 1H, CHO).

a-4-2) Fmoc-NH—NHCH$_2$(C$_6$H$_4$)OCH$_2$OEt:

5.6 g of Fmoc cabazate (22 mmol) is added with stirring to a solution of 4-(ethoxymethoxy)-benzaldehyde (5.3 g, 29 mmol) in 100 ml of dry THF at ambient temperature. After 10 mins, 1 g of molecular sieve (4 Å) is added and the mixture is stirred for 1 hr. 1.57 g of sodium cyanoborohydride (25 mmol) is added over 45 mins and the pH is maintained at 3-4 by addition of a solution of HCl (2N). After 2 hrs stirring, the pH is adjusted to 1. 50 ml of ethyl acetate are then added and the mixture is neutralized with a saturated solution of NaHCO$_3$. The aqueous phase is extracted with CH$_2$Cl$_2$ (3×50 ml). The organic phases are dried over Na$_2$SO$_4$ and the solvent is evaporated under reduced pressure to give an oil which on addition of petroleum ether gives a white precipitate (5.34 g, 58%).

Mp: 113° C. $^1$H NMR (CDCl$_3$): 1.30 (t, 3H, J=7.1 Hz, CH$_3$), 3.70 (q, 2H, J=7.1 Hz, CH$_2$), 3.98 (d, 2H, J=6.8 Hz, CH$_2$), 4.25 (t, 1H, J=6.8 Hz, CH), 4.50 (d, 2H, J=6.8 Hz, CH$_2$), 5.25 (s, 2H, CH$_2$), 6.30 (brs, 1H, NH), 7.15-7.80 (m, 13H, ar), 8.21 (brs, 1H, NH). $^{13}$C NMR (CDCl$_3$): 157.49, 144.06, 141.76, 130.70, 128.19, 127.50, 125.40, 120.44, 116.68, 93.58, 67.36, 64.65, 55.48, 47.60, 15.53. Anal. Calc: C$_{25}$H$_{26}$N$_2$O$_4$: 418.1892. C, 71.74; H, 6.27; N, 6.70; Theor: C, 71.78; H, 6.29; N, 6.70.

a-4-3) Fmoc-N$^α$hTyr (OCH$_2$OEt)-OH:

The monomer Fmoc-N$^α$hTyr (OCH$_2$OEt)-OH is prepared following the general procedure of reductive amination from the hydrazine Fmoc-NH—NHCH$_2$(C$_6$H$_4$)OCH$_2$OEt described above $^1$H NMR (CDCl$_3$): 1.25 (t, 3H, J=7.0 Hz, CH$_3$), 3.68 (q, 2H, J=7.0 Hz, CH$_2$), 3.70 (s, 2H, CH$_2$), 4.05 (s, 2H, CH$_2$), 4.20 (t, 1H, J=6.8 Hz, CH), 4.50 (d, 2H, J=6.8 Hz, CH$_2$), 5.26 (s, 2H, CH$_2$), 6.80 (brs, 1H, NH), 7.25-7.80 (m, 8H, ar), 8.60 (brs, 1H, NH), 9.80 (br s, 1H, OH). $^{13}$C NMR (CDCl$_3$): 173.40, 157.68, 156.02, 143.93, 141.74, 131.04, 128.23, 127.55, 125.43, 120.43, 116.73, 93.48, 66.30, 64.68, 61.11, 59.00, 47.51, 15.61. HRMS [M+H]$^+$ C$_{27}$H$_{29}$N$_2$O$_6$ Calc: 477.2026; Theor: 477.2023. Anal. Calc: C, 68.04; H, 5.93; N, 5.88; Theor: C, 68.00; H, 5.90; N, 5.87.

a-5) Fmoc aza-β$^3$ Arginine (Fmoc-N$^α$hArg (Boc)-OH)

a-5-1) 1-tert-Butoxycarbonylamino-3,3-diethoxypropane:

A mixture of di-tert-butyl dicarbonate (9 g, 40 mmol.) in dioxane (40 ml) is added drop by drop, with stirring and at 0° C., to a solution of 1-amino-3,3-diethoxypropane (5.52 g, 37 mmol) and Et$_3$N (4.04 g, 40 mmol) in 5 ml dioxane. After 2 hrs, the mixture is stirred at ambient temperature for 12 hrs then the solvent is evaporated. The residual oil is taken up in 10 ml of water, acidified with 30 ml HCl (1%), then extracted with ethyl acetate (60 ml×3). The organic phases are dried (MgSO4) and evaporated to give 8.89 g of 1-tert-butoxycarbonylamino-3,3-diethoxypropane (90%).

$^1$H NMR (CDCl$_3$): 1.20 (t, 6H, J=8.8 Hz, CH$_3$), 1.40 (s, 9H, C(CH$_3$)$_3$), 1.60-2.00 (m, 2H, CH$_2$C), 3.00-3.80 (m, 6H, OCH$_2$+NHCH$_2$), 4.50 (t, 1H, J=6.4 Hz, CH), 5.05-5.10 (br, 1H, NH).

a-5-2) 3-tert-Butoxycarbonylaminopropanal:

A solution of 1-tert-butoxycarbonyl-amino-3,3-diethoxypropane (8.89 g, 36 mmol) in 15 ml of acetic acid and 4 ml of water at ambient temperature for 10 hrs, then neutralized with NaHCO$_3$, taken up in ethyl acetate and washed with brine. The organic phases are evaporated at reduced pressure to give 5.17 g of 3-tert-butoxycarbonylaminopropanal (83%).

$^1$H NMR (CDCl$_3$): 1.45 (s, 9H, C(CH$_3$)$_3$), 2.60-2.80 (t, 2H, CCH$_2$), 3.20-3.50 (m, 2H, NCH$_2$), 5.10-5.20 (br s, 1H, NH), 9.86 (s, 1H, CHO).

a-5-3) Fmoc-NH—NH(CH$_2$)$_3$NHBoc:

5.08 g of Fmoc carbazate (20 mmol) is added with stirring to a solution of 3-tert-butoxycarbonylaminopropanal (3.46 g, 20 mmol) in 100 ml of dry THF at ambient temperature. After 10 mins, 1 g of molecular sieve (4 Å) is added and the reaction mixture is stirred for 12 hrs. 1.26 g of sodium cyanoborohydride (20 mmol) is added in portions over 45 mins. The pH is maintained at 3-4 by addition of a 2N solution of HCl. The mixture is stirred for a further 2 hrs, then the pH is adjusted to 1.50 mL of ethyl acetate are then added to the mixture, and the solution is neutralized with NaHCO$_3$. The mixture is extracted with CH$_2$Cl$_2$ (3×50 ml). The organic phases are dried (Na$_2$SO$_4$) and the solvent is evaporated to give an oil which crystallizes on addition of petroleum ether (4.27 g, 52%).

mp: 101° C. $^1$H NMR (DMSO) 1.40 (s, 9H, tBu), 1.50 (m, 2H, CH$_2$), 2.68 (m, 2H, CH$_2$), 2.98 (m, 2H, CH$_2$), 4.24 (t, 1H, J=6.9 Hz, CH), 4.32 (d, 2H, J=6.9 Hz, CH$_2$), 4.70-4.85 (brs, 1H, NH), 6.78 (brs, 1H, NH), 6.80 (brs, 1H, NH), 7.25-7.90 (m, 8H, ar). $^{13}$C NMR (DMSO) 157.21, 155.95, 144.18, 142.94, 127.98, 127.64, 125.59, 120.46, 77.71, 65.82, 47.08, 38.39, 28.62, 28.21. HRMS calc C$_{23}$H$_{29}$N$_3$O$_4$: 411.2158 Anal Calc C$_{23}$H$_{29}$N$_3$O$_4$: C, 67.12; H, 7.11; N, 10.22. Theor: C, 67.22; H, 7.19; N, 10.24.

a-5-4) Benzyl aza-β$^3$-(Boc)homolysinate

K$_2$CO$_3$ (802 mg, 5.8 mmol) is added to a solution of Fmoc protected hydrazine Fmoc-NH—NH(CH$_2$)$_3$NHBoc obtained in the preceding stage (3.7 g, 9 mmol) and of benzyl 2-bromoacetate (2.66 g, 11.6 mmol) in 20 ml of toluene. The mixture is brought to reflux with stirring for 28 hrs. The solution is filtered and evaporated under vacuum. The crude product is chromatographed on silica gel (ethyl acetate/hexane 1/3) to give 3.02 g (60%) of benzyl aza-β$^3$-(Boc)homolysinate in the form of an oil which slowly precipitates.

mp: 107° C. $^1$H NMR (CDCl$_3$) 1.50 (s, 9H, tBu), 1.62 (m, 2H, CH$_2$), 2.97 (m, 2H, CH$_2$), 3.24 (m, 2H, CH$_2$), 3.75 (m, 2H, CH$_2$), 4.20 (t, 1H, J=6.9 Hz, CH), 4.50 (d, 2H, J=6.9 Hz, CH$_2$), 5.19 (s, 2H, CH$_2$), 6.88 (brs, 1H, NH), 7.25-7.90 (m, 13H, Ar). $^{13}$C NMR (CDCl$_3$): 171.23, 156.55, 155.50, 144.13, 141.77, 135.54, 129.13, 129.04, 128.84, 128.14, 127.47, 125.44, 120.40, 79.38, 67.09, 64.47, 57.63, 54.56, 47.67, 38.83, 28.85, 27.83. HRMS calc.: C$_{32}$H$_{37}$N$_3$O$_6$: 559.2682. Anal calc. C$_{32}$H$_{37}$N$_3$O$_6$: C, 68.66; H, 6.67; N, 7.51. Theor: C, 68.59; H, 6.86; N, 7.28.

a-5-5) Benzyl aza-β$^3$-homolysinate 2 mL of TFA are added to a solution of benzyl aza-β$^3$-(Boc) homolysinate (0.56 g, 1 mmol) in 4 mL of DCM, and the solution is stirred for 6 hrs at ambient temperature. Evaporation under reduced pressure gives benzyl aza-β$^3$-homolysinate (0.41 g, 92%) in the form of an oil.

a-5-6) Benzyl aza-β$^3$-arginate (N-Boc)

The benzyl aza-β$^3$-homolysinate (0.18 g, 0.40 mmol) in solution in 5 ml of CH$_2$Cl$_2$ is slowly added to a solution of (BocNH)$_2$C═NTf (0.16 g, 0.41 mmol) [(BocHN)$_2$C═NTf is prepared according to the method of Feichtinger, K; Zapf, C; Sings, H. L; Goodman, M. *J. Org. Chem.* 1998, 63, 3804] and of triethylamine (0.64 ml, 0.46 mmol). After stirring at ambient temperature for 12 hrs, the solution is washed with a saturated solution of NaHCO$_3$ (25 ml) and the aqueous phase is extracted with CH$_2$Cl$_2$ (3×50 ml). The combined organic phases are dried over Na$_2$SO$_4$ and concentrated in vacuo. The crude product, purified by flash chromatography (ethyl acetate/hexane 1/2), gives 0.23 g of benzyl aza-$\beta^3$-arginate (N-Boc) (85%).

mp: 70-72° C. $^1$H NMR (CDCl$_3$) 1.39 (s, 18H, tBu), 1.60 (m, 2H, CH$_2$), 2.80 (m, 2H, CH$_2$), 3.32 (m, 2H, CH$_2$), 3.66 (m, 2H, CH$_2$), 4.24 (t, 1H, J=7.1 Hz, CH), 4.45 (d, 2H, J=7.1 Hz, CH$_2$), 5.05 (s, 2H, CH$_2$), 6.95 (brs, 1H, NH), 7.27-7.82 (m, 13H, Ar), 8.28 (brs, 1H, NH), 11.45 (brs, 1H, NH). $^{13}$C NMR (CDCl$_3$): 171.45, 170.80, 163.97, 156.57, 153.59, 144.17, 141.73, 135.67, 129.06, 128.91, 128.78, 128.09, 127.45, 125.47, 120.34, 83.35, 79.48, 66.93, 60.74, 58.04, 53.89, 47.64, 38.83, 28.67, 28.44, 27.45. HRMS C$_{38}$H$_{47}$N$_5$O$_8$ Calcd. 701.3424 Anal. Calcd for C$_{38}$H$_{47}$N$_5$O$_8$ C, 65.02; H, 6.75; N, 9.98. Found: C, 65.10; H, 6.83; N, 9.98.

a-5-7) FmocN$^\alpha$hArg(Boc)-OH:

30 mg of 10% Pd/C are added to a solution of benzyl $\beta^3$-arginate (N-Boc) (0.35 g, 0.5 mmol) in 25 ml of ethanol under an atmosphere of hydrogen. The mixture is stirred at ambient temperature for 6 hrs. The catalyst is filtered off on celite. The celite is washed with EtOH (3×15 ml) and the filtrate is evaporated to give 0.26 g (89%) of aza-$\beta^3$-arginine (N-Boc) in the form of an oil which slowly crystallizes.

Mp: 94° C. $^1$H NMR (CDCl$_3$) 1.38 (s, 9H, tBu), 1.39 (s, 9H, tBu), 1.62 (m, 2H, CH$_2$), 2.89 (m, 2H, CH$_2$), 3.38 (m, 2H, CH$_2$), 3.60 (m, 2H, CH$_2$), 4.14 (t, 1H, J=7.1 Hz, CH), 4.40 (d, 2H, J=7.1 Hz, CH$_2$), 7.27-7.82 (m, 8H, Ar), 7.95 (br s, 1H, NH), 8.50 (br s, 1H, NH), 11.50 (br s, 1H, NH). $^{13}$C NMR (CDCl$_3$): 171.35, 170.70, 163.90, 157.45, 153.57, 143.96, 141.75, 128.18, 127.52, 127.31, 125.44, 120.38, 83.35, 79.60, 67.42, 58.04, 53.89, 47.61, 38.83, 28.59, 28.46, 27.47. HRMS calc for C$_{31}$H$_{41}$N$_5$O$_8$ (M+) 611.2955. Theor (M+) 611.2958. Anal. Calc. for C$_{31}$H$_{41}$N$_5$O$_8$: C, 60.85; H, 6.76; N, 11.45. Theor. C, 60.95; H, 6.78; N, 11.47.

a-6) Fmoc aza-$\beta^3$-Lysine (Fmoc-N$^\alpha$hLys-OH)

a-6-1) 1-tert-Butoxycarbonylamino-3,3-diethoxybutane:

A mixture of di-tert-butyl dicarbonate (9.6 g, 40 mmol.) in dioxane (40 ml) is added drop by drop, with stirring and at 0° C., to a solution of 1-amino-3,3-diethoxybutane (5.9, 37 mmol) and Et$_3$N (4.04 g, 40 mmol) in 5 ml dioxane. After 2 hrs, the mixture is stirred at ambient temperature for 12 hrs then the solvent is evaporated. The residual oil is taken up in 10 mL of water, acidified with 30 ml HCl (1%), then extracted with ethyl acetate (60 ml×3). The organic phases are dried (MgSO$_4$) and evaporated to give 9.4 g of 1-tert-butoxycarbonylamino-3,3-diethoxybutane (90%).

$^1$H NMR (CDCl$_3$): 1.20 (t, 6H, J=8.8 Hz, CH$_3$), 1.40 (s, 9H, C(CH$_3$)$_3$), 1.60-1.80 (m, 2H, CH$_2$C), 3.15 (m, 2H NCH$_2$), 3.48 (m, 2H, OCH$_2$), 3.85 (m, 2H, OCH$_2$), 4.45 (t, 1H, J=6.4 Hz, CH), 4.65-4.70 (br, 1H, NH).

a-6-2) 3-tert-Butoxycarbonylaminobutanal:

A solution of 1-tert-butoxycarbonylamino-3,3-diethoxybutane (1.61 g, 6.2 mmol) in 12 ml of acetic acid and 6 ml of water is stirred at ambient temperature for 5 hrs, then neutralized with NaHCO$_3$, taken up in ethyl acetate and washed with brine. The organic phases are evaporated under reduced pressure, to give 1.27 g of an oil corresponding to 3-tert-butoxycarbonylaminobutanal in equilibrium with the hydroxy-2 pyrazolidine.

$^1$H NMR (CDCl$_3$): 1.40 (s, 9H, C(CH$_3$)$_3$), 1.70-2.00 (m, 4H, CH$_2$), 3.20-3.50 (m, 2H, CH$_2$), 5.30-5.40 (br s, 1H, NH), 9.86 (s, CHO).

a-6-3) Fmoc-NH—NH(CH$_2$)$_4$ NHBoc:

5.08 g of Fmoc carbazate (20 mmol) is added with stirring to a solution of 3-tert-butoxycarbonylaminobutanal (3.46 g, 20 mmol) in 100 ml of dry THF at ambient temperature. After 10 mins, 1 g of molecular sieve (4 Å) is added and the reaction mixture is stirred for 12 hrs. 1.26 g of sodium cyanoborohydride (20 mmol) is added in portions over 45 mins. The pH is maintained at 3-4 by addition of a 2N solution of HCl. The mixture is stirred for a further 2 hrs, then the pH is adjusted to 1.50 mL of ethyl acetate are then added to the mixture, and the solution is neutralized with NaHCO$_3$. The mixture is extracted with CH$_2$Cl$_2$ (3×50 ml). The organic phases are dried (Na$_2$SO$_4$) and the solvent is evaporated to give an oil that crystallizes on addition of petroleum ether (4.27 g, 52%).

84%. mp: 149° C. $^1$H NMR (DMSO): 1.45 (s, 9H, tBu), 1.55 (m, 4H, 2CH$_2$), 2.90 (m, 2H, CH$_2$), 3.20 (m, 2H, CH$_2$), 4.25 (t, 1H, J=6.8 Hz, CH), 4.50 (d, 2H, J=6.8 Hz, CH$_2$), 4.65 (br s, 1H, NH), 6.45 (br s, 1H, NH), 7.30-7.85 (m, 8H, ar). $^{13}$C NMR (DMSO): 158.53, 156.06, 144.13, 141.07, 128.00, 127.41, 125.55, 120.44, 77.73, 65.82, 50.05, 47.05, 40.52, 28.58, 27.47, 24.93. Anal. Calc: C$_{24}$H$_{31}$N$_3$O$_4$ 425.2314 C, 67.73; H, 7.35; N, 9.88; Theor: C, 67.70; H, 7.33; N, 9.87.

a-6-4) Fmoc-N$^\alpha$hLys (Boc)-OH:

The monomer Fmoc-N$^\alpha$hLys(Boc)-OH is prepared following the general procedure of reductive amination from the hydrazine Fmoc-NH—NH(C$_2$)$_4$ NHBoc described above 82%. $^1$H NMR (CDCl$_3$): 1.45 (s, 9H, tBu), 1.55 (m, 4H, 2 CH$_2$), 3.10 (m, 2H, CH$_2$), 3.60 (m, 2H, CH$_2$), 4.25 (t, 1H, J=6.8 Hz, CH), 4.50 (d, 2H, J=6.8 Hz, CH$_2$), 4.80 (br s, 1H, NEI), 6.90 (br s, 1H, NH), 7.30-7.85 (m, 8H, ar). $^{13}$C NMR (CDCl$_3$): 170.97, 156.49, 156.00, 144.17, 141.76, 128.84, 128.14, 125.4 g, 120.40, 79.38, 67.04, 58.00, 56.52, 47.64, 40.53, 28.83, 27.68, 25.01. HRMS C$_{26}$H$_{33}$N$_3$O$_6$ [M+Na]$^+$ Calc: 506.2267; Theor: 506.2265.

a-7) Fmoc-aza-$\beta^3$-Asparagine (Fmoc-N$^\alpha$hAsn(Trt)-OH).

a-7-1) Boc NH—NHCH$_2$CONH$_2$:

Boc carbazate (4.23 g; 0.95 eq) is added to a solution of methyl glyoxalate (3 g; 33.6 mmol) in DCM (50 ml). The reaction mixture is left for 12 hrs with stirring at ambient temperature and is concentrated to give a pasty solid directly reduced by catalytic hydrogenation in methanol (30 ml) in presence of Pd/C (200 mg) for 20 hrs. The reaction mixture is concentrated then a 6N ammoniacal methanol solution (13 ml) is added. The reaction mixture is left with stirring for 48 hrs at ambient temperature then concentrated. In the presence of diethyl ether, the oil precipitates to give the expected product in the form of a white solid (4.27 g, 70%).

$^1$H NMR (CDCl$_3$) δ ppm: 1.49 (s, 9H, CH$_3$); 3.56 (s, 2H, CH$_2$); 5.88 (brs, 1H, NH); 6.43 (s, 1H, NH amide); 7.33 (s, 1H, NH amide).

a-7-2) Boc-Aza-$\beta^3$-Asn-OBn:

To a solution of amide (7.1 g; 37 mmol) in a 1/1 toluene/DMF mixture (70 ml) are successively added K$_2$CO$_3$ (4.6 g; 0.7 eq) and benzyl bromoacetate (17.10 g; 2 eq). The reaction mixture is left with stirring at 50° C. for 5 days then it is concentrated and taken up into 100 mL of DCM. After two washings with water (2×50 ml), the organic phase is dried over Na$_2$SO$_4$ then concentrated to give a paste. Trituration in diethyl ether gives a white powder (5.35 g; 42%) corresponding to the expected product.

$^1$H NMR (CDCl$_3$) 8 ppm: 1.45 (s, 9H, CH$_3$); 3.61 (s, 2H, CH$_2$); 3.77 (s, 2H, CH$_2$); 5.21 (s, 2H, CH$_2$); 5.50 (brs, 1H, NH); 6.94 (s, 1H, NH amide); 7.33-7.45 (m, 5H, Ar); 8.18 (s, 1H, NH amide).

$^{13}$C NMR (CDCl$_3$) δ ppm: 28.2 ($\underline{C}$H$_3$); 58.58 ($\underline{C}$H$_2$N); 60.89 (CH$_2$N); 67.03 ($\underline{C}$O$_2$CH$_2$); 81.23 (C(CH$_3$); 128.47 128.71 128.75 134.92 (C Ar); 155.75 (Boc $\underline{C}$O); 170.32 ($\underline{C}$O$_2$Bn); 172.68 ($\underline{C}$ONH$_2$).

a-7-3) Fmoc-Aza-$\beta^3$-Asn-OBn:

Gaseous HCl is bubbled into a solution of BocAza-$\beta^3$-AsnOBn (6.40 g) in 100 mL of DCM: The reaction mixture is left with stirring for 1 night at ambient temperature then concentrated. The white solid obtained is triturated in ether, then filtered. It is treated with triethylamine (2.30 g; 1.2 eq) in DCM (60 ml). The clear solution is concentrated to give a pasty solid directly dissolved in a 1/1 water/THF mixture (100 ml). NaHCO$_3$ (3.19 g; 2 eq) is added as well as a solution of FmocCl (5.88 g; 1.2 eq) in THF (50 ml) drop by drop. The reaction mixture is left with stirring for 24 hrs at ambient temperature. After addition of diethyl ether (75 ml) the organic phase is recovered and washed with a saturated aqueous solution of NaCl. The organic phase is dried over Na$_2$SO$_4$ then concentrated to give a brown oil. The crude product is purified by chromatography on silica gel (DCM/AcOEt 3/7 and 1/9) to recover the expected product in the form of a white powder (g; %).

$^1$H NMR (CDCl$_3$) δ ppm: 3.62 (s, 2H, CH$_2$); 3.76 (s, 2H, CH$_2$); 4.21 (t, 1H, CH Fmoc); 4.47 (d, 2H, CH$_2$ Fmoc); 5.23 (s, 2H, CH$_2$); 5.42 (brs, 1H, NH); 7.16 (s, 1H, NH amide); 7.28-7.56 (m, 9H, Ar); 7.56 (d, 2H, Ar); 7.78 (d, 2H, Ar); 7.94 (s, 1H, NH amide).

$^{13}$C NMR (CDCl$_3$) δ ppm: 49.24 (CH Fmoc); 60.51 (CH$_2$N); 62.80 (CH$_2$N); 69.19 (CH$_2$ Fmoc); 69.37 (CO$_2$ CH$_2$); 122.17 127.09 129.24 129.96 130.54 130.63 130.66 130.71 137.00 143.44 145.58 (C Ar); 158.56 (Fmoc CO); 172.29 (CO$_2$Bn); 174.32 (CONH$_2$).

a-7-4) Fmoc-Aza-β$^3$-Asn(NHTrt)-OBn:

To a solution of Fmoc-Aza-β$^3$-Asn(NHTrt)-OBn (180 mg, 0.4 mmol) in 2 mL of AcOH are successively added triphenylmethanol (102 mg, 1 eq), acetic anhydride (80 mg, 2 eq) and 2 μL of concentrated H$_2$SO$_4$. The reaction mixture, with stirring, is heated to 55° C. for 1 hour then allowed to cool to ambient temperature. The reaction mixture is concentrated to ⅓ of its volume, and 10 mL of ice water are added. After extraction with AcOEt, the organic phase is washed with water and with a saturated aqueous solution of NaCl. The organic phase is dried over Na$_2$SO$_4$ then concentrated. The oil obtained is purified by chromatography on silica gel (AcOEt/PE) to recover 140 mg (50%) of expected product in the form of a white solid.

NMR 1H(CDCl$_3$) δ ppm: 3.70 (s, 2H, CH$_2$); 3.82 (s, 2H, CH$_2$); 4.12 (t, 1H, CH Fmoc); 4.26 (d, 2H, CH$_2$ Fmoc); 5.24 (s, 2H, CH$_2$); 7.28-7.60 (m, 26H, Ar); 7.81 (d, 2H, Ar); 9.47 (s, 1H, NH).

a-8) Fmoc-aza-β$^3$-Proline (Fmoc-N"hPro-OH).

a-8-1) ZNH—NHBoc:

An aqueous solution of NaOH (2.4 g, 1 eq in 60 mL of water) is added to a solution of Boc carbazate (7.93 g, 60 mmol) in 60 mL of CHCl$_3$. The mixture is cooled in an ice bath and a solution of benzyl chloroformate (10.24 g, 1 eq) in CHCl$_3$ (60 ml) is added slowly, then the mixture is maintained at ambient temperature with stirring for 12 hrs. The organic phase is then washed with water and brine then dried over Na$_2$SO$_4$. After evaporation of the solvent, the white solid obtained is taken up in petroleum ether and filtered off (14.17 g, 89%).

a-8-2) Benzyl-pyrazolidine-1-carboxylate:

NaH (80% in oil, 1.21 g, 2.1 eq) is added at 0° C. to a solution of doubly protected hydrazine (5.33 g, 20 mmol) in DMF (40 ml). After stirring of the reaction mixture for 30 mins at ambient temperature, 1,3-dibromopropane (4.04 g, 1 eq) is added and the mixture is stirred for 12 hrs. The mixture is poured into water (80 ml) and extracted twice with AcOEt (2×75 ml). The organic phase is washed with water and brine and dried over Na$_2$SO$_4$. After evaporation of the solvent, the mixture is purified on a column by chromatography on silica gel (PE-AcOEt 75-25) and gives 5.00 g of benzyl tert-butyl pyrazolidine-1,2-dicarboxylate (82%), which is then deprotected by dissolution (5.00 g, 16.3 mmol) in 50 mL DCM and saturation with HClg. After 12 hrs of stirring at ambient temperature, the mixture is concentrated and taken up in 30 mL of water. AcOEt (70 ml) is added and the solution is neutralised by addition of a saturated solution of NaHCO$_3$. The organic phase is washed with water, dried over Na$_2$SO$_4$, and concentrated to give a colorless oil (3.30 g, 98%).

a-8-3) Z-Aza-β$^3$-Proline tert-butyl ester:

K$_2$CO$_3$ (1.55 g, 0.7 eq) and tert-butyl bromoacetate (4.68 g, 1.5 eq) are added to a solution of benzyl-pyrazolidine-1-carboxylate (3.30 g, 16 mmol) in toluene (40 ml). The mixture is stirred for 4 days at 75° C. then filtered. The filtrate is then washed with water and brine, then dried over Na$_2$SO$_4$. After evaporation of the solvent, the oil obtained is purified on a silica gel chromatography column (PE-AcOEt 70-30) to give 4.35 g of Z-Aza-β$^3$-proline tert-butyl ester in the form of an oil (85%).

$^1$H NMR (CDCl$_3$): 1.49 (s, 9H, CH$_3$), 2.16 (q, 2H, CH$_2$), 3.24 (t, 2H, CH$_2$), 3.51 (s, 2H, CH$_2$), 3.65 (t, 2H, CH$_2$), 5.22 (s, 2H, CH$_2$), 7.30-7.49 (m, 5H, Ar).

$^{13}$C NMR (CDCl$_3$): 26.11 CH$_2$, 29.74 CH$_3$, 47.09 54.97 60.22 N—CH$_2$, 68.85 CH$_2$, 83.06 C(CH$_3$)$_3$, 127.83 127.89 128.40 138.37 Car, 157.05 COCH$_2$, 170.39 CO.

a-8-4) Aza-β$^3$-Proline tert-butyl ester:

10% Pd/C (80 mg) is added to a solution of Z-Aza-β$^3$-Proline tert-butyl ester (1.00 g, 3.12 mmol) in MeOH (10 ml). The mixture is left with stirring under an atmosphere of hydrogen for 12 hrs (progress monitored by TLC). The catalyst is filtered off on celite and the filtrate is evaporated; 0.58 g (99%) of Aza-β$^3$-Proline tert-butyl ester are obtained in the form of an oil.

$^1$H NMR (CDCl$_3$): 1.50 (s, 9H, CH$_3$), 2.01 (q, 2H, CH$_2$), 2.90 (t, 2H, CH$_2$), 3.03 (t, 2H, CH$_2$), 3.39 (brs, 1H, NH), 3.51 (s, 2H, CH$_2$).

a-8-5) Fmoc-Aza-β$^3$-Proline tert-butyl ester:

To a solution of Aza-β$^3$-Proline tert-butyl ester (0.58 g, 3.12 mmol) in THF/water (10/5 ml), with stirring, are added NaHCO$_3$ (0.52 g, 2 eq) then drop by drop a solution of FmocCl (0.97 g, 1.2 eq) in THF (10 ml). After stirring for 12 hrs at ambient temperature, ether (50 ml) is added and the organic phase is taken, washed with brine, dried over Na$_2$SO$_4$, then evaporated. The oil obtained is purified on a silica gel chromatography column (PE/EtOAc 9/1 and 6/4). 1.00 g (79%) of Fmoc-Aza-β$^3$-Proline tert-butyl ester are obtained in the form of an oil.

$^1$H NMR (CDCl$_3$): 1.52 (s, 9H, CH$_3$), 2.18 (q, 2H, CH$_2$), 3.27 (t, 2H, CH$_2$), 3.55 (s, 2H, CH$_2$), 3.65 (t, 2H, CH$_2$), 4.33 (t, 1H, CH Fmoc), 4.46 (d, 2H, CH$_2$ Fmoc), 7.30-7.88 (m, 8H, Ar).

a-8-6) Fmoc-Aza-β$^3$-Proline:

A solution of Fmoc-Aza-β$^3$-Proline test-butyl ester (1.00 g, 2.5 mmol) in 10 ml of DCM is saturated with HClg then stirred at ambient temperature for 5 hrs. The solvent is evaporated, the mixture is taken up in water (20 ml), then a solution of NaHCO$_3$ (N) is added until the pH is basic. The aqueous phase is extracted with ether, acidified with 2N HCl, then extracted with AcOEt. The organic phase is washed with brine and dried over Na$_2$SO$_4$. After evaporation of the solvent the solid obtained is triturated in petroleum ether; Fmoc-Aza-β$^3$-Proline (0.64 g, 74%) is obtained in the form of a white solid. Mp: 130° C.

$^1$H NMR (CDCl$_3$): 2.01 (q, 2H, CH$_2$), 2.89 (t, 2H, CH$_2$), 3.34 (s, 2H, CH$_2$), 3.35 (t, 2H, CH$_2$), 4.15 (t, 1H, CH Fmoc), 4.47 (d, 2H, CH$_2$ Fmoc), 7.30-7.88 (m, 8H, Ar).

$^{13}$C NMR (CDCl$_3$): 24.10 CH$_2$, 43.47 N—CH$_2$, 45:94 CH Fmoc, 54.12 59.98 N—CH$_2$, 67.08 CH$_2$ Fmoc, 118.80, 123.63, 125.95, 126.67, 140.13, 142.12 Car, 157.15 CO Fmoc, 169.70 COOH.

HRMS [M+Na]$^+$ $C_{20}H_{20}N_2O_4Na$ calc: 375.13208; theor. 375.1320.

b) Peptide Synthesis: Hybrid Peptides

The monomers described above can, in the same way as a protected amino acid, be integrated into selected positions of a peptide by synthesis on a solid support using a Fmoc strategy automatic synthesizer in order to obtain hybrid peptides. They can also be combined to give oligomers constituted exclusively of aza-β$^3$-amino acid units.

The synthesis of the hybrid peptides was effected in accordance with the following scheme:

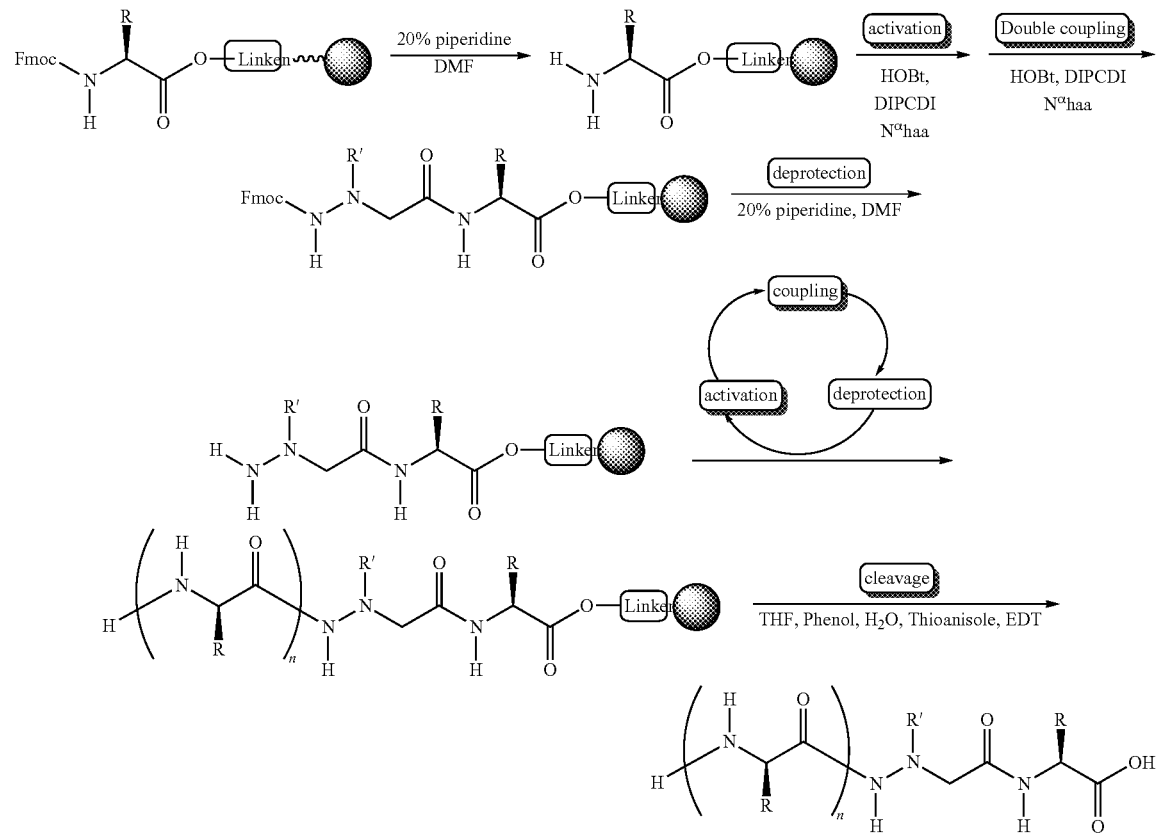

The synthesis of the peptide analogues was performed using a Milligen PepSyntheziser™ model 9050 automatic synthesizer operating by the Fmoc strategy in continuous flow condition. The functional groups of the side-chains of the Fmoc-amino acids are protected with the following protective groups: a t-butoxycarbonyl (Boc) group for lysine (Lys), t-butyl (tBu) for tyrosine (Tyr) and threonine (Thr), triphenylmethyl (Trt) for glutamine (Gln) and 2,2,4,5,6-pentamethyldihydrobenzofuran-5-sulfonyl (Pbf) for arginine (Arg). The DMF must not contain any amine capable of deprotecting the Fmoc group in the course of the synthesis and the piperidine used for the deprotection steps is 99% pure. Diisopropylcarbodiimide (DIPCDI) and 1-hydroxybenzotriazole (HOBt) are used as coupling agents.

The resin (1.00 g) preloaded (at ~0.2 mmol/g) with an amino acid or aza-β$^3$-amino acid residue is placed in the synthesizer reactor. The couplings are effected with four times the stoichiometric amount of amino acid or aza-β$^3$-amino acid and a coupling time of 30 mins, and, depending on the amino acids or the aza-β$^3$-amino acids utilized, a double coupling or a coupling time of 60 mins is necessary. After each coupling step and at the end of synthesis, the N-terminal end of the last residue attached is deprotected automatically with a 20% solution of piperidine in DMF.

The cleavage from the resin and the deprotection of the functional groups of the side-chains are effected simultaneously by the action of the reagent K (82.5% TFA, 5% phenol, 5% water, 5% thioanisole and 2.5% ethanedithiol). The resin is taken out of the reactor and rinsed with dichloromethane, then dried in the desiccator. It is placed in a flask then the freshly prepared cleavage cocktail K is added and the reaction mixture is left with stirring for 3 hrs at ambient temperature. The solution containing the hybrid peptide is then recovered by filtration of the resin on a fritted filter. After evaporation of the solvent under reduced pressure to a volume of about 2 ml, the crude hybrid peptide is isolated by precipitation in iced ether and filtration on a fritted filter. It is purified by HPLC on a C18 reverse phase column (250×4.6 mm) using an elution gradient (solvent A: water+0.1% TFA and solvent B acetonitrile+0.08% TFA) 0% B to 70% B in 20 mins then 70% B to 0% B in 5 mins, with a flow rate of 1.2 mL/min. The UV detection is performed at 210 nm. The purity of the hybrid peptides synthesized is checked by mass spectrometry by the ESI technique in an acetonitrile/water mixture (50/50).

88-99H4

The synthesis of analogues of the peptide 88-99 of the histone H4, for which we have successfully replaced different positions, was performed using this methodology. For example, the monomers Ala, Leu, Lys, Tyr, Gly were replaced by their respective analogue N$^\alpha$hAla, N$^\alpha$hLeu, N$^\alpha$hLys, N$^\alpha$hTyr, N$^\alpha$hGly etc . . . .

Peptide 88-99 of the histone H4:
H-Tyr-Ala-Leu-Lys-Arg-Gln-Gly-Arg-Thr-Leu-Tyr-Gly-OH Examples of hybrid peptides prepared:

SEQ ID NO: 2 (or peptide E):
$^{88}$H$_2$N-Tyr-Ala-Leu-Lys-Arg-Gln-Gly-Arg-Thr-Nα-hLeu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 3 (or peptide C):
$^{88}$H$_2$N-Tyr-Ala-Nα-hLeu-Lys-Arg-Gln-Gly-Arg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 4 (or peptide A):
$^{88}$H$_2$N-Tyr-Nα-hAla-Leu-Lys-Arg-Gln-Gly-Arg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 5 (or peptide B):
$^{88}$H$_2$N-Tyr-Nα-hAla-Nα-hLeu-Lys-Arg-Gln-Gly-Arg-Thr-Leu-Tyr-Gly-OH$^{99}$
[M + H]$^+$ = 1455.8 (theoretical [M + H]$^+$ = 1440.8) and doubly charged ion peak [M + 2H]$^{++}$ = 728.4.

SEQ ID NO: 6 (or peptide D):
$^{88}$H$_2$N-Tyr-Ala-Leu-Nα-hLys-Arg-Gln-Gly-Arg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 7 (or peptide G):
$^{88}$H$_2$N-Tyr-Ala-Leu-Lys-Arg-Gln-Gly-Arg-Thr-Nα-hLeu-Nα-hTyr-Gly-OH$^{99}$
[M + H]$^+$ = 1455.8 (theoretical [M + H]$^+$ = 1440.8) and doubly charged ion peak [M + 2H]$^{++}$ = 728.4.

SEQ ID NO: 8:
$^{88}$H$_2$N-Tyr-Ala-Leu-Lys-Arg-Gln-Nα-hGly-Arg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 9:
$^{88}$H$_2$N-Tyr-Ala-Leu-Lys-Arg-Gln-Gly-Nα-hArg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 10:
$^{88}$H$_2$N-Tyr-Ala-Leu-Lys-Nα-hArg-Gln-Gly-Arg-Thr-Leu-Tyr-Gly-OH$^{99}$
[M + H]$^+$ = 1440.8 (theoretical [M + H]$^+$ = 1440.8) and doubly charged ion peak [M + 2H]$^{++}$ = 720.9.

SEQ ID NO: 11:
$^{88}$H$_2$N-Tyr-Ala-Leu-Lys-Arg-Gln-Gly-Arg-Thr-Leu-Nα-hTyr-Gly-OH$^{99}$
[M + H]$^+$ = 1440.8 (theoretical [M + H]$^+$ = 1440.8) and doubly charged ion peak [M + 2H]$^{++}$ = 720.

SEQ ID NO: 12 (or peptide F):
$^{88}$H$_2$N-Nα-hTyr-Ala-Leu-Lys-Arg-Gln-Gly-Arg-Thr-Leu-Tyr-Gly-OH$^{99}$
[M + H]$^+$ = 1440.8 (theoretical [M + H]$^+$ = 1440.8) and doubly charged ion peak
[M + 2H]$^{++}$ = 720.9.

SEQ ID NO: 13 (or peptide H):
$^{88}$H$_2$N-Tyr-Ala-Leu-Lys-Arg-Gln-Gly-Arg-Thr-Leu-Tyr-Nα-hGly-OH$^{99}$
[M + H]$^+$ = 1440.8 (theoretical [M + H]$^+$ = 1440.8) and doubly charged ion peak
[M + 2H]$^{++}$ = 720.9.

SEQ ID NO: 14 (or peptide I):
$^{88}$H$_2$N-Tyr-Ala-Leu-Lys-Arg-Gln-Gly-Arg-Thr-Nα-hLeu-Nα-hTyr-Nα-hGly-OH$^{99}$
[M + H]$^+$ = 1470.8 (theoretical [M + H]$^+$ = 1470.8) and doubly charged ion peak
[M + 2H]$^{++}$ = 735.9.

B) Biological Analyses

BALB/c mice were immunized with the parent peptide 88-99H4 and in cell cultures the T lymphocytes of these mice were restimulated with the same peptide or with the analogues A-E. The cell proliferation was measured by the incorporation of tritiated thymidine and the index of stimulation (IS) relative to the wells without peptide was calculated. The tests are performed in triplicate and the experiment is performed several times in independent experiments. The initial results (see FIG. 1) show that one of the modified peptides, namely the analogue E (IS of 7.7 to 90 μM) has an activity analogous, or even superior depending on the experiments, to that of the parent peptide (IS of 6.7 to 90 μM).

Figure 2:
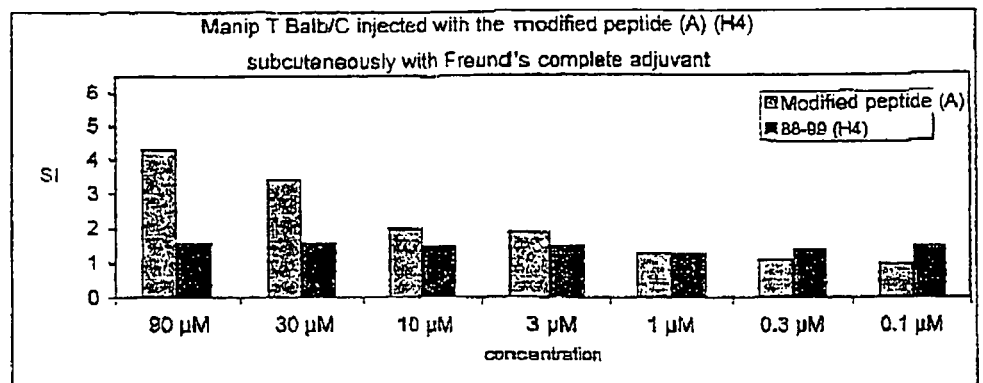
Figure 2:
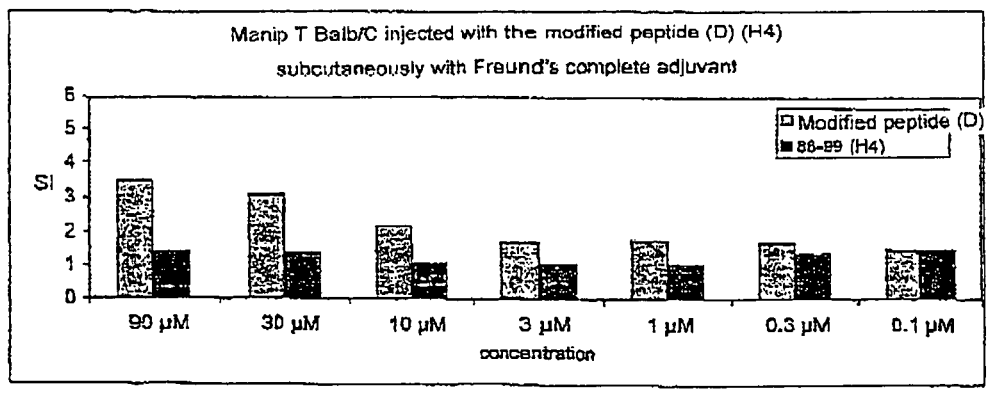

In addition, a mirror manipulation of the foregoing was performed, namely response tests on the T lymphocytes of mice injected with the modified peptides and stimulation ex vivo with the parent peptide (88-99). After injection of the analogues, analyses were performed on cell cultures with the said analogues and the parent peptide 88-99. The following results are observed:

1) peptides A and D are immunogenic (induce responses against the homologous peptide) but with no cross reaction with the parent peptide (see FIG. 2).

Figure 3:
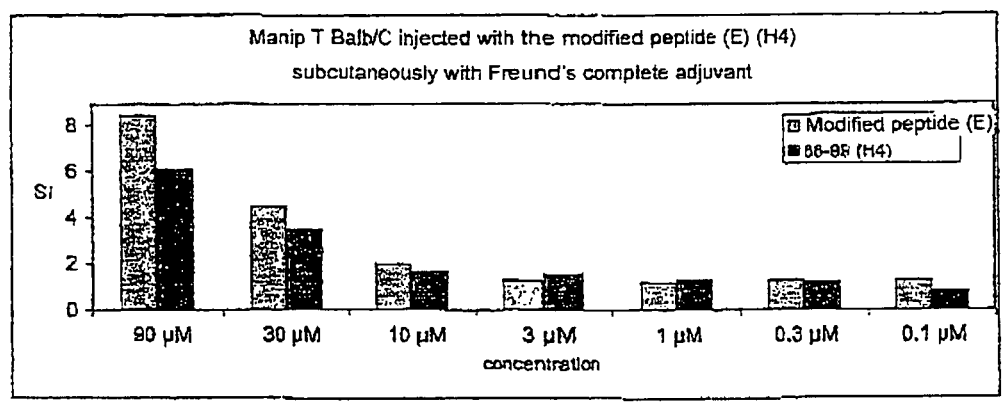

2) peptide E is immunogenic and the T cells generated react by cross reaction with the parent peptide (see FIG. 3).

Peptide E cross reacts perfectly with the parent peptide 88-99.

The same experiments were performed with peptide G, (corresponding to the sequence SEQ ID NO: 7).

The results (see FIG. 4) show that the analogue G (IS of 16.6 to 100 μM) has an activity analogous to that of the parent peptide (IS of 16.9 to 100 μM).

In addition, a mirror experiment of the foregoing was performed, namely an experiment on mice injected with the peptide G and stimulation ex vivo with increasing quantities of the parent peptide (88-99). It is observed that the peptide G is immunogenic and that the T cells generated against this peptide react by cross reaction with the homologous peptide G and in particular with the parent peptide with the same intensity (see FIG. 5).

II) Hybrid Peptides of the Peptide 307-319 of the Influenza Haemagglutinin

The inventors have performed the synthesis, by a method identical to that previously described in the context of the hybrid peptides of the histone H4, of another series of hybrid peptides corresponding to a T CD4$^+$ peptide derived from the nucleoprotein of the influenza virus (peptide HA 307-319: Pro-Lys-Tyr-Val-Lys-Gln-Asn-Thr-Leu-Lys-Leu-Ala-Thr) which is part of the composition of a synthetic vaccine preparation currently being tested for its neutralizing and protective properties.

The peptides synthesized are as follows:

sured by the incorporation of tritiated thymidine and the index of proliferation (IS) relative to the wells with no peptide was calculated. The tests are performed in triplicate and the experiment is performed several times in independent experiments. Among the analogous peptides tested, the results show that the peptide J' (IS of 21.8 to 100 µM) has an activity clearly superior to that of the parent peptide (see FIG. 6).

In addition a mirror experiment of the foregoing was performed, namely an experiment on mice injected with the modified peptides and stimulation ex vivo with the parent peptide (307-319). Thus, after injection of the analogous peptide, analyses were performed on cell cultures with the different analogues and the parent peptide 307-319. Among the peptides tested, the following results are observed:

1) peptides L' and I' are immunogenic (induce responses against the homologous peptide, and against the parent peptide).

2) the best candidate is peptide J', it is immunogenic and the T cells generated react with the homologous peptide J' and by cross reaction with the parent peptide. This cross reaction is even greater than that measured with the homologous peptide SEQ ID NO: 16 (or peptide A'):
$^{307}$H$_2$N-Nα-hPro-Lys-Tyr-Val-Lys-Gln-Asn-Thr-Leu-Lys-Leu-Ala-Thr-OH$^{319}$
[M + H]$^+$ = 1518.901 (theoretical [M + H]$^+$ = 1518.90079)

SEQ ID NO: 17 (or peptide B'):
$^{307}$H$_2$N-Pro-Nα-hLys-Tyr-Val-Lys-Gln-Asn-Thr-Leu-Lys-Leu-Ala-Thr-OH$^{319}$
[M + H]$^+$ = 1518.9009 (theoretical [M + H]$^+$ = 1518.90079)

SEQ ID NO: 18 (or peptide C'):
$^{307}$H$_2$N-Pro-Lys-Nα-hTyr-Val-Lys-Gln-Asn-Thr-Leu-Lys-Leu-Ala-Thr-OH$^{319}$
[M + H]$^+$ = 1518.9008 (theoretical [M + H]$^+$ = 1518.90079)

SEQ ID NO: 19 (or peptide D'):
$^{307}$H$_2$N-Pro-Lys-Tyr-Nα-hVal-Lys-Gln-Asn-Thr-Leu-Lys-Leu-Ala-Thr-OH$^{319}$
[M + H]$^+$ = 1518.9008 (theoretical [M + H]$^+$ = 1518.90079).

SEQ ID NO: 20 (or peptide E'):
$^{307}$H$_2$N-Pro-Lys-Tyr-Val-Nα-hLys-Gln-Asn-Thr-Leu-Lys-Leu-Ala-Thr-OH$^{319}$
[M + H]$^+$ = 1518.9009 (theoretical [M + H]$^+$ = 1518.90079)

SEQ ID NO: 21 (or peptide F'):
$^{307}$H$_2$N-Pro-Lys-Tyr-Val-Lys-Gln-Asn-Thr-Nα-hLeu-Lys-Leu-Ala-Thr-OH$^{319}$
[M + H]$^+$ = 1518.9008 (theoretical [M + H]$^+$ = 1518.90079)

SEQ ID NO: 22 (or peptide G'):
$^{307}$H$_2$N-Pro-Lys-Tyr-Val-Lys-Gln-Asn-Thr-Leu-Nα-hLys-Leu-Ala-Thr-OH$^{319}$
[M + H]$^+$ = 1518.9009 (theoretical [M + H]$^+$ = 1518.90079)

SEQ ID NO: 23 (or peptide H'):
$^{307}$H$_2$N-Pro-Lys-Tyr-Val-Lys-Gln-Nα-hAsn-Thr-Leu-Lys-Leu-Ala-Thr-OH$^{319}$
[M + H]$^+$ = (theoretical [M + H]$^+$ = 1518.90079)

SEQ ID NO: 24 (or peptide I'):
$^{307}$H$_2$N-Pro-Lys-Tyr-Val-Lys-Gln-Asn-Thr-Leu-Lys-Nα-hLeu-Ala-Thr-OH$^{319}$
[M + Na]$^+$ = 1540.8816 (theoretical [M + Na]$^+$ = 1540.88273)

SEQ ID NO: 25 (or peptide J'):
$^{307}$H$_2$N-Pro-Lys-Tyr-Val-Lys-Gln-Asn-Thr-Leu-Lys-Leu-Nα-hAla-Thr-OH$^{319}$
[M + H + 2Na]$^+$ = 1562.8647 (theoretical [M + H + 2Na]$^+$ = 1562.86468)

SEQ ID NO: 26 (or peptide K'):
$^{307}$H$_2$N-Pro-Lys-Tyr-Val-Lys-Gln-Asn-Thr-Leu-Nα-hLys-Nα-hLeu-Nα-hAla-Thr-OH$^{319}$
[M + H]$^+$ = 1548.9228 (theoretical [M + H]$^+$ = 1548.92259).

SEQ ID NO: 27 (or peptide L'):
$^{307}$H$_2$N-Pro-Lys-Tyr-Val-Lys-Gln-Asn-Thr-Leu-Lys-Nα-hLeu-Nα-hAla-Thr-OH$^{319}$
[M + H]$^+$ = 1533.9090 (theoretical [M + H]$^+$ = 1533.91169).

Figure 7:
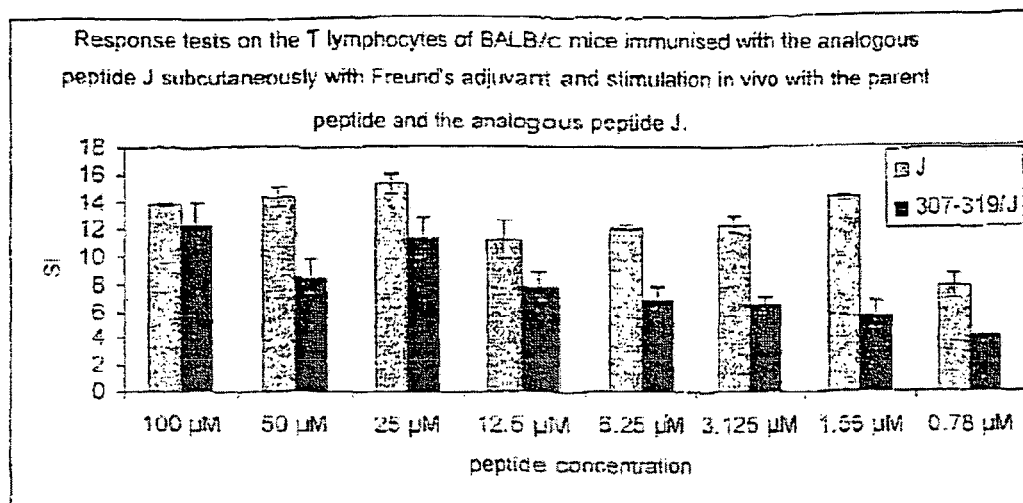

Just as before, BALB/c mice were immunized with the parent peptide 307-319 HA and in cell cultures the T lymphocytes of these mice were restimulated with the same peptide or with its analogues. The cell proliferation was measured (FIG. 7). Thus we again find the peptide J which cross reacts perfectly with the parent peptide 307-319, which confirms that the modified peptide J' is therefore an excellent candidate (see FIG. 7).

Captions of Figures:

FIG. 1: Response tests on the T lymphocytes of BALB/c mice injected with the parent peptide 88-99 of the histone H4 subcutaneously with Freund's adjuvant, and stimulation ex-vivo with the parent peptide or the analogue E; the stimulation index is shown on the y-axis and the different concentrations of peptide are shown on the x-axis.

FIG. 2: Response tests on the T lymphocytes of BALB/c mice injected with the modified peptide 88-99 A or with the modified peptide 88-99 D of the histone H4 subcutaneously with Freund's adjuvant. The stimulation index is shown on the y-axis and the different concentrations of peptide are shown on the x-axis.

FIG. 3: Response tests on the T lymphocytes of BALB/c mice injected with the modified peptide 88-99 E of the histone H4 subcutaneously with Freund's adjuvant. The stimulation index is shown on the y-axis and the different concentrations of peptide are shown on the x-axis.

Figure 4:
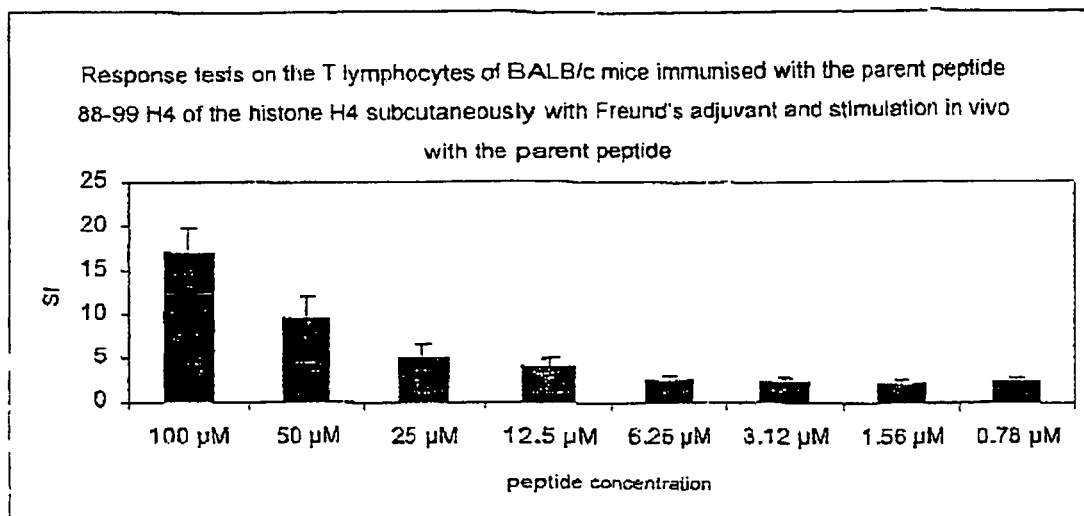
Figure 4:
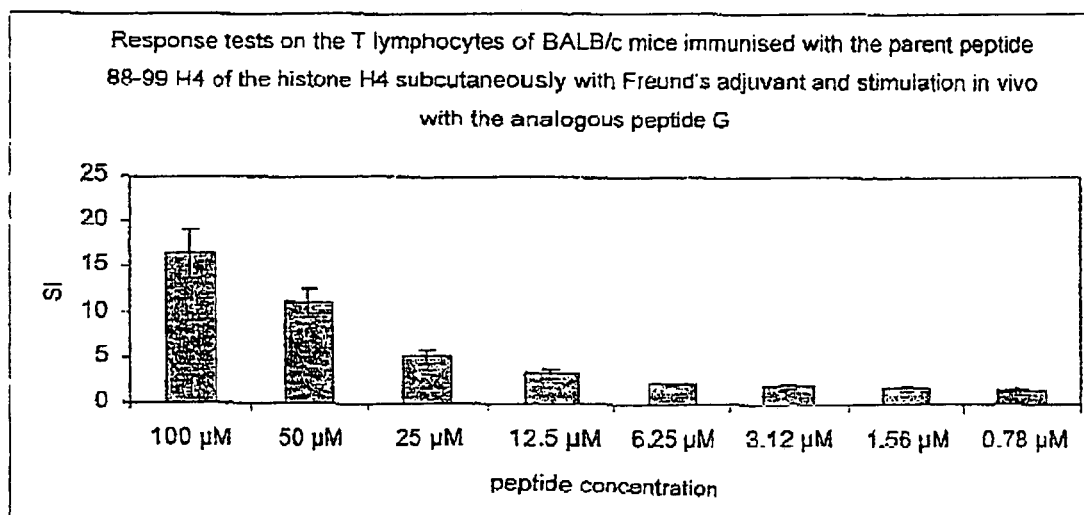

FIG. 4: Response tests on the T lymphocytes of BALB/c mice injected with the parent peptide 88-99 of the histone H4 subcutaneously with Freund's adjuvant, and stimulation ex-vivo with the parent peptide or the analogue G; the stimulation index is shown on the y-axis and the different concentrations of peptide are shown on the x-axis.

Figure 5:
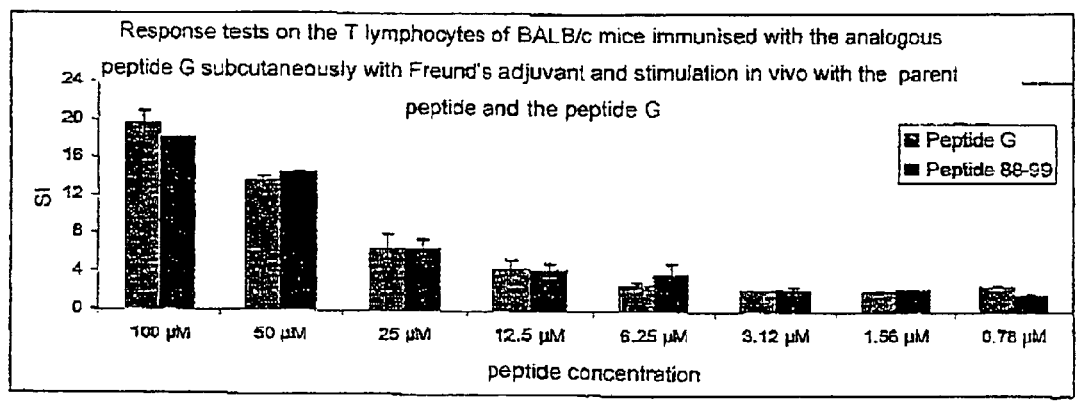

FIG. 5: Response tests on the T lymphocytes of BALB/c mice injected with the modified peptide 88-99 G of the histone H4 subcutaneously with Freund's adjuvant. The stimulation index is shown on the y-axis and the different concentrations of peptide are shown on the x-axis.

Figure 6:
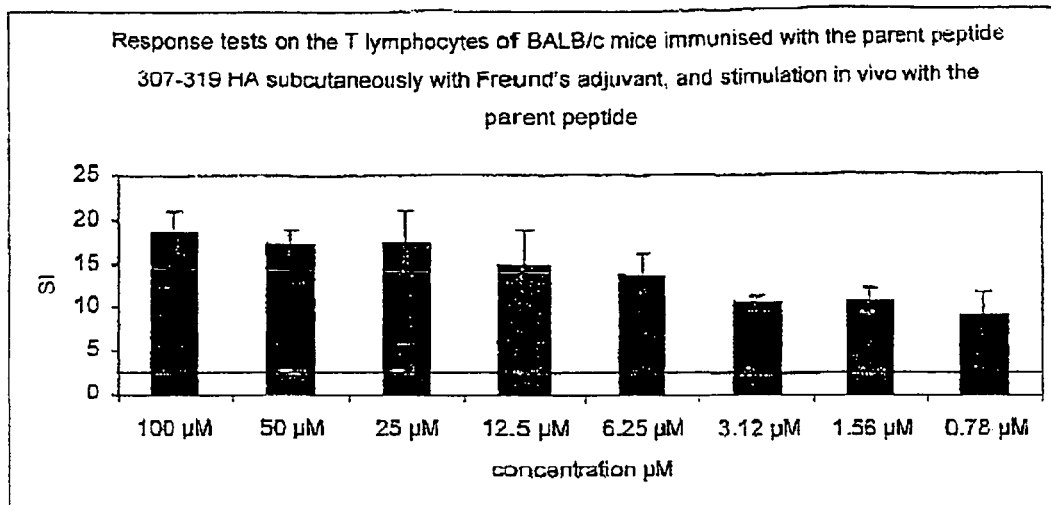
Figure 6:
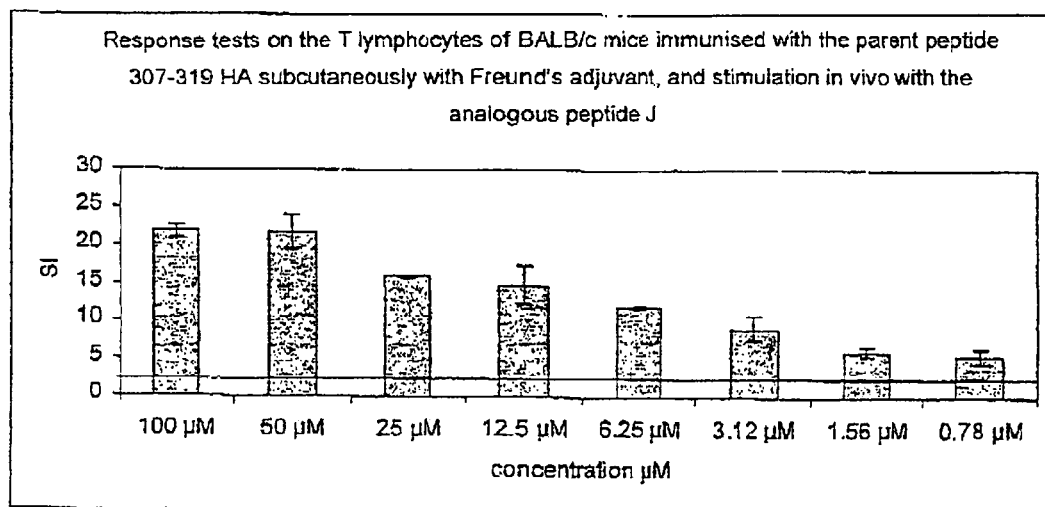

FIG. 6: Response tests on the T lymphocytes of BALB/c mice injected with the parent peptide 307-319 HA subcutaneously with Freund's adjuvant, and stimulation ex vivo with the parent peptide or the analogue J'; the stimulation index is shown on the y-axis and the different concentrations of peptide are shown on the x-axis.

FIG. 7: Response tests on the T lymphocytes of BALB/c mice immunized with the analogous peptide J subcutaneously with Freund's adjuvant, and stimulation ex vivo with the parent peptide and the analogue J'; the stimulation index is shown on the y-axis and the different concentrations of peptide are shown on the x-axis.

BIBLIOGRAPHY

Appella, E.; Loftus, D. J.; Sakaguchi, K.; Celis, E. *Biomed. Pept. Proteins Nucleic Acids* 1996, 1, 177.

Mézière, C.; Viguier, M.; Dumortier, H.; Lo-Man, R.; Leclerc, C.; Guillet, J. G.; Briand, J. P.; Muller, S. *J. Immunol.* 1997, 3230-3237.

Briand, J. P.; Benkirane, N.; Guichard, G.; Newman, J. F. E.; Van Regenmortel, M. H. V.; Brown, F.; Muller, S. *Proc. Natl. Acad. Sci. U.S.A.* 1997, 94, 12545-12550.

Liu, M. A. *Nat. Med.*, 1998, 4, Suppl. 5, 503.

Stemmer, C.; and Guichard, G. *Exp. Opin. Ther. Patents* 1998, 8, 819-830.

Ostankovitch, M, Guichard, G, Connan, F, Muller, S, Chaboissier, A, Hoebeke, J, Choppin, J, Briand, J P, Guillet, J G. *J Immunol* 1998; 161:200-8.

Petit, M. C.; Benkirane, N.; Guichard, G.; Phan Chan Du, A.; Marraud, M.; Cung, M. T.; Briand, J. P.; Muller, S. *J. Biol. Chem.* 1999, 274, 3686-3692.

Stemmer, C.; Quesnel, A.; Prevost-Blondel, A.; Zimmermann, C.; Muller, S.; Briand, J. P.; Pircher, H. *J. Biol. Chem.* 1999, 274, 5550-5555

Ben Yedidia, T., Beignon, A S, Partidos, C D, Muller, S, and Amon, A. *Mol. Immunol.* 2002, 39, 323-331.

Phan-Chan Du, A., Limal, D., Semetey, V., Dali, H., Jolivet, M., Desgranges, C., Cung, M T, Briand, J P, Petit, M C and Muller, S. *J. Mol Biol.* 2002, 323, 503-521.

Decker, P., Le Moal, A., Briand, J. P., Muller, S. *J. Immunol.* 2000, 165, 654-662.

The invention claimed is:

1. A method for the treatment of systemic lupus erythematosus, comprising administering to a patient in need thereof a pharmaceutically acceptable amount of a hybrid peptide containing at least one aza-$\beta^3$ aminoacyl residue, selected from the group consisting of:

a residue corresponding to formula (A) when the residue is situated at the N-terminal position,

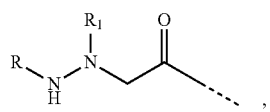

wherein R represents H or a protective group of the amine function of the amino acids, and $R_1$ represents an amino acid side-chain, a residue corresponding to formula (B) when the residue is situated at the C-terminal position,

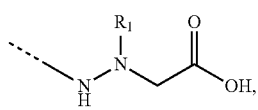

wherein $R_1$ represents an amino acid side-chain and a residue corresponding to formula (C) when the residue is situated in the chain of the hybrid peptides,

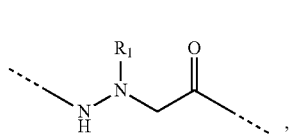

wherein $R_1$ represents an amino acid side-chain, wherein said hybrid peptide comprises amino acids 88-99 of histone H4 (SEQ ID NO: 1), and at least one of said amino acids is replaced by the aza-$\beta^3$ amino acid analogue residue.

2. The method according to claim 1, comprising administering a pharmaceutically acceptable amount of a hybrid peptide of formula (I):

$$aa_l\text{-}N^\alpha haa_m\text{-}aa_n\text{-}N^\alpha haa_o\text{-}aa_p \quad (I)$$

wherein:

$aa_l$, $aa_n$ and $aa_p$ represent an aminoacyl residue, or a concatenation of aminoacyl residues, corresponding to the aminoacyl residues present at the same positions in the peptide or parent protein from which the hybrid peptides are derived, $N^\alpha haa_m$ and $N^\alpha haa_o$ represent an aza-$\beta^3$ aminoacyl monomer residue, or a concatenation of aza-$\beta^3$ aminoacyl monomer residues, analogous to the aminoacyl residues initially present at the same position in the peptide or the parent protein from which the hybrid peptides are derived, the aza-$\beta^3$ aminoacyl monomers corresponding to the formulae (A), (B), or (C), depending on whether the aza-$\beta^3$ aminoacyl monomers are respectively positioned at the N-terminal or C-terminal, or in the chain of the hybrid peptides, and wherein $R_1$ is identical to the side-chain of the initial amino acid of the peptide or parent protein to which the aza-$\beta^3$ aminoacyl monomers correspond, and l, m, n, o, and p represent a whole number from 0 to 20 inclusive, provided that at least one of m and o is not zero, and that the minimum number of residues in the hybrid peptides of formula (I) is 4.

3. The method according to claim 1, wherein the hybrid peptide comprises one or more of:

(SEQ ID NO: 2)
$^{88}$H$_2$N-Tyr-Ala-Leu-Lys-Arg-Gln-Gly-Arg-Thr-N-hLeu-Tyr-Gly-OH$^{99}$;

(SEQ ID NO: 3)
$^{88}$H$_2$N-Tyr-Ala-N-hLeu-Lys-Arg-Gln-Gly-Arg-Thr-Leu-Tyr-Gly-OH$^{99}$;

(SEQ ID NO: 4)
$^{88}$H$_2$N-Tyr-N-hAla-Leu-Lys-Arg-Gln-Gly-Arg-Thr-Leu-Tyr-Gly-OH$^{99}$;

(SEQ ID NO: 5)
$^{88}$H$_2$N-Tyr-N-hAla-N-hLeu-Lys-Arg-Gln-Gly-Arg-Thr-Leu-Tyr-Gly-OH$^{99}$;

(SEQ ID NO: 6)
$^{88}$H$_2$N-Tyr-Ala-Leu-N-hLys-Arg-Gln-Gly-Arg-Thr-Leu-Tyr-Gly-OH$^{99}$;

(SEQ ID NO: 7)
$^{88}$H$_2$N-Tyr-Ala-Leu-Lys-Arg-Gln-Gly-Arg-Thr-N-hLeu-N-hTyr-Gly-OH$^{99}$;

(SEQ ID NO: 8)
$^{88}$H$_2$N-Tyr-Ala-Leu-Lys-Arg-Gln-N-hGly-Arg-Thr-Leu-Tyr-Gly-OH$^{99}$;

(SEQ ID NO: 9)
$^{88}$H$_2$N-Tyr-Ala-Leu-Lys-Arg-Gln-Gly-N-hArg-Thr-Leu-Tyr-Gly-OH$^{99}$;

(SEQ ID NO: 10)
$^{88}$H$_2$N-Tyr-Ala-Leu-Lys-N-hArg-Gln-Gly-Arg-Thr-Leu-Tyr-Gly-OH$^{99}$;

(SEQ ID NO: 11)
$^{88}$H$_2$N-Tyr-Ala-Leu-Lys-Arg-Gln-Gly-Arg-Thr-Leu-N-hTyr-Gly-OH$^{99}$;

(SEQ ID NO: 12)
$^{88}$H$_2$N-N-hTyr-Ala-Leu-Lys-Arg-Gln-Gly-Arg-Thr-Leu-Tyr-Gly-OH$^{99}$;

(SEQ ID NO: 13)
$^{88}$H$_2$N-Tyr-Ala-Leu-Lys-Arg-Gln-Gly-Arg-Thr-Leu-Tyr-N-hGly-OH$^{99}$;

(SEQ ID NO: 14)
$^{88}$H$_2$N-Tyr-Ala-Leu-Lys-Arg-Gln-Gly-Arg-Thr-N-hLeu-N-hTyr-N-hGly-OH$^{99}$.

4. The method according to claim 3, wherein the hybrid peptide comprises SEQ ID NO: 2, SEQ ID NO: 7, or a combination thereof.

5. A hybrid peptide containing at least one aza-$\beta^3$ amino acid, the hybrid peptide comprising amino acids 88-99 of histone H4 (SEQ ID NO: 1), wherein at least one of said amino acids 88-99 is replaced by an aza-$\beta^3$ amino acid analogue.

6. The hybrid peptide according to claim 5, of formula (I):

$$aa_l\text{-}N^\alpha haa_m\text{-}aa_n\text{-}N^\alpha haa_o\text{-}aa_p \quad (I)$$

wherein:

$aa_l$, $aa_n$ and $aa_p$ represent an aminoacyl residue, or a concatenation of aminoacyl residues, corresponding to the aminoacyl residues present at the same positions in the peptide or the parent protein from which the hybrid peptides are derived, $N^\alpha haa_m$ and $N^\alpha haa_o$ represent an aza-$\beta^3$ aminoacyl monomer residue, or a concatenation of aza-$\beta^3$ aminoacyl monomer residues, analogous to the aminoacyl residues initially present at the same position in the peptide or the parent protein from which the hybrid peptides are derived, the aza-$\beta^3$ aminoacyl monomers corresponding to:

formula (A) when the residue is situated at the N-terminal position,

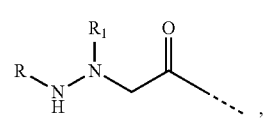

(A)

wherein R represents H or a protective group of the amine function of the amino acids, such and $R_1$ represents an amino acid side chain, formula (B) when the residue is situated at the C-terminal position,

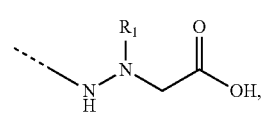

(B)

wherein $R_1$ is an amino acid side-chain, and formula (C) when the residue is situated in the chain of the hybrid peptides,

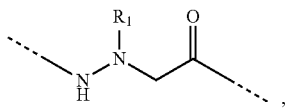

(C)

wherein R₁ is an amino acid side-chain, wherein R₁ is identical to the side-chain of the initial amino acid of the peptide or parent protein to which the aza-β³ aminoacyl monomers correspond, and wherein l, m, n, o and p represent a whole number from 0 to 20 inclusive, provided that at least one of m and o is not zero, the number of residues in the hybrid peptide of formula (I) is at least 4, and at least one of l, n, and p is not zero.

7. The hybrid peptide according to claim 5, selected from the group consisting of the following formulae:

(SEQ ID NO: 2)
⁸⁸H₂N-Tyr-Ala-Leu-Lys-Arg-Gln-Gly-Arg-Thr-N-hLeu-Tyr-Gly-OH⁹⁹;

(SEQ ID NO: 3)
⁸⁸H₂N-Tyr-Ala-N-hLeu-Lys-Arg-Gln-Gly-Arg-Thr-Leu-Tyr-Gly-OH⁹⁹;

(SEQ ID NO: 4)
⁸⁸H₂N-Tyr-N-hAla-Leu-Lys-Arg-Gln-Gly-Arg-Thr-Leu-Tyr-Gly-OH⁹⁹;

(SEQ ID NO: 5)
⁸⁸H₂N-Tyr-N-hAla-N-hLeu-Lys-Arg-Gln-Gly-Arg-Thr-Leu-Tyr-Gly-OH⁹⁹;

(SEQ ID NO: 6)
⁸⁸H₂N-Tyr-Ala-Leu-N-hLys-Arg-Gln-Gly-Arg-Thr-Leu-Tyr-Gly-OH⁹⁹;

(SEQ ID NO: 7)
⁸⁸H₂N-Tyr-Ala-Leu-Lys-Arg-Gln-Gly-Arg-Thr-N-hLeu-N-hTyr-Gly-OH⁹⁹;

(SEQ ID NO: 8)
⁸⁸H₂N-Tyr-Ala-Leu-Lys-Arg-Gln-N-hGly-Arg-Thr-Leu-Tyr-Gly-OH⁹⁹;

(SEQ ID NO: 9)
⁸⁸H₂N-Tyr-Ala-Leu-Lys-Arg-Gln-Gly-N-hArg-Thr-Leu-Tyr-Gly-OH⁹⁹;

(SEQ ID NO: 10)
⁸⁸H₂N-Tyr-Ala-Leu-Lys-N-hArg-Gln-Gly-Arg-Thr-Leu-Tyr-Gly-OH⁹⁹;

(SEQ ID NO: 11)
⁸⁸H₂N-Tyr-Ala-Leu-Lys-Arg-Gln-Gly-Arg-Thr-Leu-N-hTyr-Gly-OH⁹⁹;

(SEQ ID NO: 12)
⁸⁸H₂N-N-hTyr-Ala-Leu-Lys-Arg-Gln-Gly-Arg-Thr-Leu-Tyr-Gly-OH⁹⁹;

(SEQ ID NO: 13)
⁸⁸H₂N-Tyr-Ala-Leu-Lys-Arg-Gln-Gly-Arg-Thr-Leu-Tyr-N-hGly-OH⁹⁹;

(SEQ ID NO: 14)
⁸⁸H₂N-Tyr-Ala-Leu-Lys-Arg-Gln-Gly-Arg-Thr-N-hLeu-N-hTyr-N-hGly-OH⁹⁹.

8. A complex comprising the hybrid peptide as defined in claim 5 and an element of the major histocompatibility complex, and optionally a T cell receptor.

9. A complex comprising the hybrid peptide as defined in claim 5 and a T cell receptor.

10. A pharmaceutical composition or vaccine, comprising:
the hybrid peptide as defined in claim 5, or
an anti-idiotype antibody capable of forming a complex with polyclonal or monoclonal anti-hybrid peptide antibodies,
the anti-hybrid peptide antibody being capable of forming a complex with the hybrid peptide, and/or with the peptide or parent protein corresponding to these latter, wherein they recognize the parent peptide or the parent protein with an affinity at least equal to that of the anti-parent peptide or anti-parent protein antibodies towards the parent peptide or the parent protein,
in combination with a physiologically acceptable vehicle.

11. A pharmaceutical composition for treating a pathology comprising:
the hybrid peptide as defined in claim 5, or
an anti-idiotype antibody capable of forming a complex with polyclonal or monoclonal anti-hybrid peptide antibodies, the anti-hybrid peptide antibodies being capable of forming a complex with the hybrid peptide, and/or with the peptide or parent protein corresponding to these latter, wherein they recognize the parent peptide or the parent protein with an affinity at least equal to that of the anti-parent peptide or anti-parent protein antibodies towards the parent peptide or the parent protein, combined with a carrier molecule capable of inducing in vivo the production of antibodies for neutralizing an exogenous or endogenous protein responsible for the pathology, or capable of inducing in vivo a cytotoxic or helper cellular immune response.

12. A pharmaceutical composition, comprising:
a polyclonal or monoclonal anti-hybrid peptide antibody against the hybrid peptide defined in claim 5, the antibodies being capable of forming a complex with the hybrid peptide, and/or with the peptide or parent protein corresponding to these latter, wherein they recognize the parent peptide or the parent protein with an affinity at least equal to that of the anti-parent peptide or anti-parent protein antibodies towards the parent peptide or the parent protein, in combination with a physiologically acceptable vehicle.

13. A peptide, comprising the amino acid sequence of SEQ ID NO: 1, wherein at least one amino acid is substituted by an aza-$\beta^3$ analogue of that amino acid, and at least one amino acid is not substituted by an aza-$\beta^3$ analogue.

14. The peptide according to claim 13, comprising at least two aza-$\beta^3$ amino acids.

15. The peptide according to claim 14, wherein two aza-$\beta^3$ amino acids are separated by at least one non-substituted amino acid.

16. The peptide according to claim 14, wherein two aza-$\beta^3$ amino acids are immediately adjacent to each other.

17. The peptide according to claim 13, comprising at least three aza-$\beta^3$ amino acids.

18. The peptide according to claim 13, wherein at least one aza-$\beta^3$ amino acid is not located at the C-terminal position or the N-terminal position of the peptide.

19. The peptide according to claim 13, wherein at least one aza-$\beta^3$ amino acid is located at the C-terminal position or the N-terminal position of the peptide.

* * * * *

SEQUENCE LISTING

```
<160> NUMBER OF SEQ ID NOS: 27

<210> SEQ ID NO 1
<211> LENGTH: 12
<212> TYPE: PRT
<213> ORGANISM: Homo sapiens

<400> SEQUENCE: 1

Tyr Ala Leu Lys Arg Gln Gly Arg Thr Leu Tyr Gly
1               5                   10

<210> SEQ ID NO 2
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (10)..(10)
<223> OTHER INFORMATION: Nalpha-hLeucine

<400> SEQUENCE: 2

Tyr Ala Leu Lys Arg Gln Gly Arg Thr Xaa Tyr Gly
1               5                   10

<210> SEQ ID NO 3
<211> LENGTH: 12
<212> TYPE: PRT
<213> ORGANISM: Artificial sequence
```

```
<220> FEATURE:
<223> OTHER INFORMATION: Hybrid peptide
<220> FEATURE:
<221> NAME/KEY: MISC_FEATURE
<222> LOCATION: (3)..(3)
<223> OTHER INFORMATION: Nalpha-hLeucine

<400> SEQUENCE: 3

Tyr Ala Xaa Lys Arg Gln Gly Arg Thr Leu Tyr Gly
1               5                   10

<210> SEQ ID NO 4
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (2)..(2)
<223> OTHER INFORMATION: Nalpha-hAlanine

<400> SEQUENCE: 4

Tyr Xaa Leu Lys Arg Gln Gly Arg Thr Leu Tyr Gly
1               5                   10

<210> SEQ ID NO 5
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (2)..(2)
<223> OTHER INFORMATION: Nalpha-hAlanine
<220> FEATURE:
<221> NAME/KEY: MISC_FEATURE
<222> LOCATION: (3)..(3)
<223> OTHER INFORMATION: Nalpha-hLeucine

<400> SEQUENCE: 5

Tyr Xaa Xaa Lys Arg Gln Gly Arg Thr Leu Tyr Gly
1               5                   10

<210> SEQ ID NO 6
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (4)..(4)
<223> OTHER INFORMATION: Nalpha-hLysine

<400> SEQUENCE: 6

Tyr Ala Leu Xaa Arg Gln Gly Arg Thr Leu Tyr Gly
1               5                   10

<210> SEQ ID NO 7
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (10)..(10)
<223> OTHER INFORMATION: Nalpha-hLeucine
```

```
<220> FEATURE:
<221> NAME/KEY: MISC_FEATURE
<222> LOCATION: (11)..(11)
<223> OTHER INFORMATION: Nalpha-hTyrosine

<400> SEQUENCE: 7

Tyr Ala Leu Lys Arg Gln Gly Arg Thr Xaa Xaa Gly
1               5                   10

<210> SEQ ID NO 8
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (7)..(7)
<223> OTHER INFORMATION: Nalpha-hGlycine

<400> SEQUENCE: 8

Tyr Ala Leu Lys Arg Gln Xaa Arg Thr Leu Tyr Gly
1               5                   10

<210> SEQ ID NO 9
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (8)..(8)
<223> OTHER INFORMATION: Nalpha-hArginine

<400> SEQUENCE: 9

Tyr Ala Leu Lys Arg Gln Gly Xaa Thr Leu Tyr Gly
1               5                   10

<210> SEQ ID NO 10
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (5)..(5)
<223> OTHER INFORMATION: Nalpha-hArginine

<400> SEQUENCE: 10

Tyr Ala Leu Lys Xaa Gln Gly Arg Thr Leu Tyr Gly
1               5                   10

<210> SEQ ID NO 11
<211> LENGTH: 12
<212> TYPE: PRT
<213> ORGANISM: Artificial sequence
<220> FEATURE:
<223> OTHER INFORMATION: Hybrid peptide
<220> FEATURE:
<221> NAME/KEY: MISC_FEATURE
<222> LOCATION: (11)..(11)
<223> OTHER INFORMATION: Nalpha-hTyrosine

<400> SEQUENCE: 11

Tyr Ala Leu Lys Arg Gln Gly Arg Thr Leu Xaa Gly
1               5                   10
```

```
<210> SEQ ID NO 12
<211> LENGTH: 12
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (1)..(1)
<223> OTHER INFORMATION: Nalpha-hTyrosine

<400> SEQUENCE: 12

Xaa Ala Leu Lys Arg Gln Gly Arg Thr Leu Tyr Gly
1               5                   10

<210> SEQ ID NO 13
<211> LENGTH: 12
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (12)..(12)
<223> OTHER INFORMATION: Nalpha-hGlycine

<400> SEQUENCE: 13

Tyr Ala Leu Lys Arg Gln Gly Arg Thr Leu Tyr Xaa
1               5                   10

<210> SEQ ID NO 14
<211> LENGTH: 12
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (10)..(10)
<223> OTHER INFORMATION: Nalpha-hLeucine
<220> FEATURE:
<221> NAME/KEY: MISC_FEATURE
<222> LOCATION: (11)..(11)
<223> OTHER INFORMATION: Nalpha-hTyrosine
<220> FEATURE:
<221> NAME/KEY: MISC_FEATURE
<222> LOCATION: (12)..(12)
<223> OTHER INFORMATION: Nalpha-hGlycine

<400> SEQUENCE: 14

Tyr Ala Leu Lys Arg Gln Gly Arg Thr Xaa Xaa Xaa
1               5                   10

<210> SEQ ID NO 15
<211> LENGTH: 13
<212> TYPE: PRT
<213> ORGANISM: Homo sapiens

<400> SEQUENCE: 15

Pro Lys Tyr Val Lys Gln Asn Thr Leu Lys Leu Ala Thr
1               5                   10

<210> SEQ ID NO 16
<211> LENGTH: 13
<212> TYPE: PRT
<213> ORGANISM: Artificial sequence
<220> FEATURE:
<223> OTHER INFORMATION: hybrid peptide
```

```
<220> FEATURE:
<221> NAME/KEY: MISC_FEATURE
<222> LOCATION: (1)..(1)
<223> OTHER INFORMATION: Nalpha-hProline

<400> SEQUENCE: 16

Xaa Lys Tyr Val Lys Gln Asn Thr Leu Lys Leu Ala Thr
1               5                   10

<210> SEQ ID NO 17
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (2)..(2)
<223> OTHER INFORMATION: Nalpha-hLysine

<400> SEQUENCE: 17

Pro Xaa Tyr Val Lys Gln Asn Thr Leu Lys Leu Ala Thr
1               5                   10

<210> SEQ ID NO 18
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (3)..(3)
<223> OTHER INFORMATION: Nalpha-hTyrosine

<400> SEQUENCE: 18

Pro Lys Xaa Val Lys Gln Asn Thr Leu Lys Leu Ala Thr
1               5                   10

<210> SEQ ID NO 19
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (4)..(4)
<223> OTHER INFORMATION: Nalpha-hValine

<400> SEQUENCE: 19

Pro Lys Tyr Xaa Lys Gln Asn Thr Leu Lys Leu Ala Thr
1               5                   10

<210> SEQ ID NO 20
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (5)..(5)
<223> OTHER INFORMATION: Nalpha-hLysine

<400> SEQUENCE: 20

Pro Lys Tyr Val Xaa Gln Asn Thr Leu Lys Leu Ala Thr
1               5                   10
```

```
<210> SEQ ID NO 21
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (9)..(9)
<223> OTHER INFORMATION: Nalpha-hLeucine

<400> SEQUENCE: 21

Pro Lys Tyr Val Lys Gln Asn Thr Xaa Lys Leu Ala Thr
1               5                   10

<210> SEQ ID NO 22
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (10)..(10)
<223> OTHER INFORMATION: Nalpha-hLysine

<400> SEQUENCE: 22

Pro Lys Tyr Val Lys Gln Asn Thr Leu Xaa Leu Ala Thr
1               5                   10

<210> SEQ ID NO 23
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (7)..(7)
<223> OTHER INFORMATION: Nalpha-hAsparagine

<400> SEQUENCE: 23

Pro Lys Tyr Val Lys Gln Xaa Thr Leu Lys Leu Ala Thr
1               5                   10

<210> SEQ ID NO 24
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (11)..(11)
<223> OTHER INFORMATION: Nalpha-hLeucine

<400> SEQUENCE: 24

Pro Lys Tyr Val Lys Gln Asn Thr Leu Lys Xaa Ala Thr
1               5                   10

<210> SEQ ID NO 25
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (12)..(12)
<223> OTHER INFORMATION: Nalpha-hAlanine
```

```
<400> SEQUENCE: 25

Pro Lys Tyr Val Lys Gln Asn Thr Leu Lys Leu Xaa Thr
1               5                   10

<210> SEQ ID NO 26
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (10)..(10)
<223> OTHER INFORMATION: Nalpha-hLysine
<220> FEATURE:
<221> NAME/KEY: MISC_FEATURE
<222> LOCATION: (11)..(11)
<223> OTHER INFORMATION: Nalpha-hLeucine
<220> FEATURE:
<221> NAME/KEY: MISC_FEATURE
<222> LOCATION: (12)..(12)
<223> OTHER INFORMATION: Nalpha-hAlanine

<400> SEQUENCE: 26

Pro Lys Tyr Val Lys Gln Asn Thr Leu Xaa Xaa Xaa Thr
1               5                   10

<210> SEQ ID NO 27
<211> LENGTH: 13
<212> TYPE: PRT
<213> ORGANISM: Artificial sequence
<220> FEATURE:
<223> OTHER INFORMATION: hybrid peptide
<220> FEATURE:
<221> NAME/KEY: MISC_FEATURE
<222> LOCATION: (11)..(11)
<223> OTHER INFORMATION: Nalpha-hLeucine
<220> FEATURE:
<221> NAME/KEY: MISC_FEATURE
<222> LOCATION: (12)..(12)
<223> OTHER INFORMATION: Nalpha-hAlanine

<400> SEQUENCE: 27

Pro Lys Tyr Val Lys Gln Asn Thr Leu Lys Xaa Xaa Thr
1               5                   10
```